United States Patent

Heckmann et al.

Patent Number: 5,811,444
Date of Patent: Sep. 22, 1998

[54] COMPOSITIONS FOR REDUCING ABNORMAL STIMULATION OF ENDOTHELIN RECEPTORS AND NOVEL COMPOUNDS

[75] Inventors: Bertrand Heckmann, Cachan; Jean-Paul Vevert, Pantin; Jidong Zhang, Paris, all of France

[73] Assignee: Roussel Uclaf, France

[21] Appl. No.: 776,953

[22] PCT Filed: Aug. 1, 1995

[86] PCT No.: PCT/FR95/01034

§ 371 Date: Jan. 31, 1997

§ 102(e) Date: Jan. 31, 1997

[87] PCT Pub. No.: WO96/04276

PCT Pub. Date: Feb. 15, 1996

[30] Foreign Application Priority Data

Aug. 2, 1994 [FR] France ................................ 94 09566

[51] Int. Cl.$^6$ ........................ A61K 31/415; C07D 405/06
[52] U.S. Cl. ........................ 514/397; 514/396; 514/398; 514/399; 514/400; 548/311.7
[58] Field of Search ................... 548/311.7; 514/396, 514/397, 398, 399, 400

[56] References Cited

FOREIGN PATENT DOCUMENTS 2416012 1/1979 France .
94-02474 2/1994 WIPO .

OTHER PUBLICATIONS

Chem. Abstracts. Oct. 14, 1995, vol. 103, No. 15, C. Paul Bianchi.
Baggaley et al. Journal of Med. Chemistry, 1975, vol. 18, No. 8, 4 pgs.
Stefonich et al., Il Farmaco Ed Sc., vol. 40, No. 6, pp. 429–441 (1985).

*Primary Examiner*—Floyd D. Higel
*Attorney, Agent, or Firm*—Bierman, Muserlian and Lucas

[57] ABSTRACT

The invention relates to the new use and the new products of formula (I):

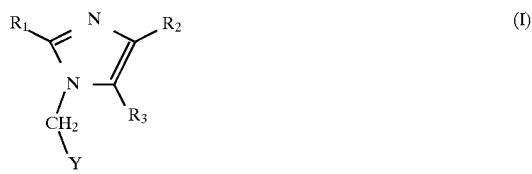

in which:

$R_1$=represents hydroxyl, alkyl, alkenyl, alkynyl, alkoxy, alkylthio, formyl, cycloalkyl, optionally interrupted by heteroatoms, $R_2$, $R_3$ represent in particular halogen, mercapto, acyl, carboxy, nitro, cyano, amino, carbamoyl, $R_4$, —$OR_4$ with $R_4$ representing in particular hydrogen, alkyl, alkenyl, alkynyl, acyl, amino, —$(CH_2)_{m1}$—$S(O)_{m2}$—X—$R_{10}$ with m1=0 to 4, m2=0 to 2, X represents a single bond or —NH—, —NH—CO—, —NH—CO—NH—, and $R_{10}$ represents alkyl, alkenyl or aryl, and Y represents optionally substituted aryl, these products being in all the isomer forms and the salts, as medicaments.

4 Claims, No Drawings

COMPOSITIONS FOR REDUCING ABNORMAL STIMULATION OF ENDOTHELIN RECEPTORS AND NOVEL COMPOUNDS

This application is a 371 of PCT/FR95/01034 filed Aug. 1, 1995.

The present invention relates to the new use of derivatives of imidazole, new derivatives of imidazole, their preparation process, the new intermediates obtained, their use as medicaments and the pharmaceutical compositions containing them.

A subject of the present invention is the use for the preparation of pharmaceutical compositions intended for the treatment of illnesses resulting from an abnormal stimulation of the endothelin receptors, of the products of formula (I):

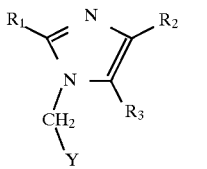

in which:
$R_1$ represents a hydroxyl, alkyl, alkenyl, alkynyl, alkoxy, alkylthio radical, each of these radicals being linear or branched and containing at most 12 carbon atoms, a formyl radical or a cycloalkyl radical optionally interrupted by one or more heteroatoms and containing 3 to 7 carbon atoms, all these radicals being optionally substituted by one or more identical or different radicals chosen from halogen atoms, the following radicals: hydroxyl, free, salified, esterified or amidified carboxy, cyano, nitro, amino optionally substituted by one or two identical or different alkyl radicals containing at most 6 carbon atoms, cycloalkyl containing 3 to 7 carbon atoms, alkyl, alkenyl and alkoxy containing at most 6 carbon atoms, haloalkyl, alkylthio, haloalkylthio, haloalkoxy, phenoxy, phenylalkoxy, optionally substituted carbamoyl, acyl, acyloxy, optionally salified tetrazolyl and phenyl optionally substituted by one or more radicals chosen from halogen atoms, hydroxyl radicals, alkyl and alkoxy radicals containing at most 4 carbon atoms, trifluoromethyl, cyano, free, salified or esterified carboxy and tetrazolyl radicals, $R_2$ and $R_3$, identical or different, are chosen from:
a) halogen atoms, the following radicals: mercapto, acyl, free, salified, esterified or amidified carboxy or carboxy-carbonyl, nitro, cyano, and the —P(O)(OR)$_2$ radical in which R represents a hydrogen atom, an alkyl or phenyl radical,
b) the $R_4$ and —OR$_4$ radicals in which:
either $R_4$ represents the —(CH$_2$)$_{m1}$—S(O)$_{m2}$—X—R$_{10}$ radical in which m1 represents an integer from 0 to 4, m2 represents an integer from 0 to 2 and either X—R$_{10}$ represents an amino radical or X represents a single bond or the —NR$_{11}$—, —NR$_{11}$—CO—, —NR$_{11}$—CO—O—, —NR$_{11}$—CO—NR$_{12}$— and —N=CR$_{11}$—NR$_{12}$— radicals and R$_{10}$ represents an alkyl, alkenyl or aryl radical, these radicals being optionally substituted by one or more identical or different radicals chosen from halogen atoms; the following radicals: hydroxyl; cycloalkyl containing 3 to 7 carbon atoms; alkyl, alkoxy, haloalkyl, alkylthio, haloalkylthio and haloalkoxy, linear or branched, containing at most 6 carbon atoms; phenoxy; phenylalkoxy; optionally substituted carbamoyl; acyl; acyloxy; free, salified or esterified carboxy; tetrazolyl; cyano; nitro; amino optionally substituted by one or two identical or different alkyl radicals containing at most 6 carbon atoms and aryl optionally substituted by one or more radicals chosen from halogen atoms, hydroxyl radicals, alkyl and alkoxy radicals containing at most 4 carbon atoms, trifluoromethyl, free, salified or esterified carboxy and tetrazolyl radicals, and $R_{11}$ and $R_{12}$, identical or different, are chosen from the hydrogen atom and the values defined for $R_{10}$, or $R_4$ represents the hydrogen atom; an alkyl, alkenyl, alkynyl and acyl radical, these radicals being linear or branched, containing at most 6 carbon atoms, and being optionally interrupted by one or more heteroatoms chosen from sulphur, oxygen or nitrogen atoms; an amino or carbamoyl radical optionally substituted by one or two identical or different alkyl or alkenyl radicals, containing at most 6 carbon atoms or the (CH$_2$)$_{m1}$—S(O)$_{m2}$—XR$_{10}$ radical as defined above; a cycloalkyl radical containing 3 to 6 carbon atoms or an aryl radical, the alkyl, alkenyl and aryl radicals of all the radicals which are represented by $R_4$ being optionally substituted by one or more identical or different radicals chosen from:
halogen atoms,
hydroxyl, mercapto, cyano, azido, nitro, —SO$_3$H, free, salified, esterified or amidified carboxy radicals,
the following radicals: alkyl, alkenyl, alkoxy, haloalkyl, alkylthio, alkenylthio, alkynylthio, acyl, acyloxy, acylthio, haloalkylthio, haloalkoxy, these radicals containing at most 6 carbon atoms, aryl, arylalkyl, arylalkenyl, arylthio, aryloxy and arylalkoxy in which the aryl radical is optionally substituted by one or more identical or different radicals chosen from halogen atoms, hydroxyl radicals, alkyl and alkoxy radicals containing at most 6 carbon atoms, haloalkyl, alkylthio, haloalkylthio, haloalkoxy, optionally substituted carbamoyl, acyl, acyloxy, free, salified or esterified carboxy, cyano, nitro, amino optionally substituted by one or two identical or different alkyl radicals containing at most 6 carbon atoms, tetrazolyl and phenyl optionally substituted by one or more radicals chosen from the halogen atoms, the following radicals: hydroxyl, alkyl and alkoxy containing at most 4 carbon atoms, trifluoromethyl, free, salified or esterified carboxy and tetrazolyl, and

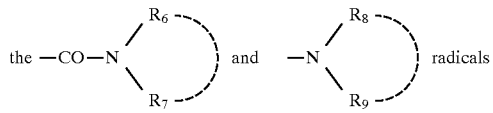

in which:
either $R_6$ and $R_7$ or $R_8$ and $R_9$, identical or different, are chosen from:
the hydrogen atom,
amino acids,
alkyl and alkenyl radicals containing at most 6 carbon atoms and optionally substituted by one or more identical or different radicals chosen from halogen atoms, the hydroxyl radical or alkoxy radicals containing at most 6 carbon atoms,
aryl, arylalkyl and arylalkenyl radicals in which the linear or branched alkyl and alkenyl radicals contain at most 6 carbon atoms, these aryl, arylalkyl and arylalkenyl radicals being optionally substituted by one or more radicals chosen from halogen atoms, hydroxyl, nitro, cyano, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified or esterified carboxy radicals, aryl and arylalkyl radicals, these last two radicals being optionally substituted by one or more radicals chosen from halogen atoms, hydroxyl, trifluoromethyl, nitro, cyano, free, salified or esterified carboxy and tetrazolyl radicals, the —$(CH_2)_{m2}$—$S(O)_{m2}$—X—$R_{10}$ radical as defined above, or $R_6$ and $R_7$ or $R_8$ and $R_9$ form respectively with the nitrogen atom to which they are linked a monocyclic radical containing 5, 6 or 7 members or a radical constituted by condensed rings containing 8 to 14 members, these identical or different radicals optionally containing one or more other heteroatoms chosen from oxygen, nitrogen and sulphur atoms, and being optionally substituted by one or more radicals chosen from halogen atoms, hydroxyl, nitro, cyano radicals, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified, esterified or amidified carboxy radicals, aryl and arylalkyl radicals, these last two radicals being optionally substituted by one or more radicals chosen from halogen atoms, hydroxyl, trifluoromethyl, nitro, cyano, free, salified or esterified carboxy and tetrazolyl radicals, or $R_8$ and $R_9$, identical or different, represent an acyl radical or one of $R_8$ or $R_9$ represents a carbamoyl, alkoxycarbonyl or benzyloxycarbonyl radical and the other is chosen from the values defined above for $R_8$ and $R_9$ or $R_8$ and $R_9$ form together with the nitrogen atom to which they are linked a phthalimido or succinimido radical, Y represents the —$Y_1$—B—$Y_2$ radical in which:

$Y_1$ represents an aryl radical optionally substituted by one or more radicals chosen from dioxol radicals and the radicals which can be represented by $R_2$ and $R_3$, B represents a single bond between $Y_1$ and $Y_2$, or one of the following divalent radicals: —CO—, —O—, —NH—CO—, —CO—NH— or —O—$(CH_2)_p$— with p representing the values 1, 2 or 3, $Y_2$ is defined as follows:

either, whatever the value of B and $Y_2$ being identical to or different from $Y_1$, $Y_2$ is chosen from the values defined for $Y_1$, or, if B represents a single bond, $Y_2$ represents a hydrogen atom, a halogen atom, a cyano radical, a free, salified, esterified or amidified carboxy radical, a tetrazolyl radical or a $(CH_2)_{m1}$—$S(O)_{m2}$—$XR_{10}$ radical as defined above, said products of formula (I) being in all the possible racemic, enantiomeric and diastereoisomeric isomer forms, as well as the addition salts with mineral and organic acids or with mineral and organic bases of said products of formula (I).

A particular subject of the present invention is the use of the products of formula (I) as defined above, for the preparation of pharmaceutical compositions intended for the treatment of hypertension induced by endothelin, any vascular spasms and for the treatment of post-cerebral haemorrhages and also for the preparation of pharmaceutical compositions intended for the treatment of myocardial infarction and for the prevention of post-angioplastic recurrence of restenosis.

In the products of formula (I) and in what follows:

the term linear or branched alkyl radical preferably designates methyl, ethyl, propyl, isopropyl, butyl, isobutyl, sec-butyl and tert-butyl radicals but can also represent a pentyl or hexyl radical and particularly isopentyl and isohexyl, the term linear or branched alkenyl radical preferably designates a vinyl, allyl, 1-propenyl, butenyl and particularly 1-butenyl, or pentenyl radical, the term linear or branched alkynyl radical preferably designates an ethynyl, propargyl, butynyl or pentynyl radical.

Among the alkyl radicals interrupted by one or more heteroatoms, there can be mentioned for example the methoxymethyl, methoxyethoxymethyl, propylthiopropyl, propyloxypropyl, propylthioethyl, methylthiomethyl radicals, the term halogen atom preferably designates the chlorine atom, but can also represent a fluorine, bromine or iodine atom, the term linear or branched alkoxy radical preferably designates the methoxy, ethoxy, propoxy or isopropoxy radicals, but can also represent a linear, secondary or tertiary butoxy radical, the term acyl radical preferably designates a radical having 1 to 6 carbon atoms such as for example the formyl, acetyl, propionyl, butyryl or benzoyl radical, but also the pentanoyl, hexanoyl, acryloyl, crotonoyl or carbamoyl radical, as well as the derivatives of carbonyl radicals such as in particular the cycloalkylcarbonyl radicals, the term acyloxy radical designates for example a radical in which the acyl radical has the values indicated above and preferably designates a formyloxy, acetyloxy, propionyloxy, butyryloxy or benzoyloxy radical, the term cycloalkyl radical optionally interrupted by one or more heteroatoms preferably designates cyclopropyl, cyclobutyl radicals and quite particularly cyclopentyl and cyclohexyl radicals or a carbocyclic radical interrupted by one or more atoms chosen from oxygen, nitrogen or sulphur atoms and quite particularly a dioxolane or dioxane radical, the term haloalkyl radical preferably designates the radicals in which the alkyl radical is as defined above and is substituted by one or more halogen atoms as defined above such as for example in bromoethyl, trifluoromethyl, trifluoroethyl or also pentafluoroethyl, the term haloalkoxy radical preferably designates the radicals in which the alkoxy radical is as defined above and is substituted by one or more halogen atoms as defined above such as for example in bromoethoxy, trifluoromethoxy, trifluoroethoxy or also pentafluoroethoxy, the term aryl radical designates an unsaturated monocyclic radical, containing 5, 6 or 7 members or a carbocyclic or heterocyclic radical constituted by condensed rings containing 8 to 14 members, it being understood that the heterocyclic radicals can contain one or more heteroatoms chosen from oxygen, nitrogen or sulphur atoms and that when these heterocyclic radicals contain more than one heteroatom, the heteroatoms of these heterocyclic radicals can be identical or different.

As examples of such an aryl radical, the following radicals can be mentioned: phenyl, naphthyl, thienyl such as 2-thienyl and 3-thienyl, furyl such as 2-furyl, pyridyl such as 2-pyridyl and 3-pyridyl, pyrimidinyl, pyrrolyl, thiazolyl, isothiazolyl, pyrazolyl, triazolyl, tetrazolyl, salified tetrazolyl, diazolyl, thiadiazolyl, thiatriazolyl, oxazolyl, oxadiazolyl, 3- or 4-isoxazolyl; condensed heterocyclic groups containing at least one heteroatom chosen from sulphur, nitrogen and oxygen, for example benzothienyl such as 3-benzothienyl, benzofuryl, benzofurannyl, benzopyrrolyl, benzimidazolyl, benzoxazolyl, thionaphthyl, indolyl, indolinyl, quinolyl or isoquinolyl, purinyl, the term arylalkyl designates the radicals in which the alkyl and aryl radicals respectively can take the values defined above for these radicals; as examples of such arylalkyl radicals, the following radicals can be mentioned: benzyl, diphenylmethyl, triphenylmethyl, naphthylmethyl, indenylmethyl, thienylmethyl such 2-thienylmethyl, furylmethyl such as furfuryl, pyridylmethyl, pyridylethyl, pyrimidylmethyl or pyrrolylmethyl, it being understood that in the non-exhaustive list of examples of radicals as mentioned above, the alkyl radical can be represented by methyl just as well as by the ethyl, propyl or butyl radicals such as, for example, in the phenylalkyl radicals such as phenylethyl, phenylpropyl or phenylbutyl;

the terms arylalkenyl and arylalkynyl designate the radicals in which the alkenyl or alkynyl and aryl radicals respectively can take the values defined above for these radicals; as examples of such arylalkenyl radicals there can be mentioned for example the examples given above of arylalkyl radicals in which the alkyl radical is replaced by an alkenyl radical such as for example in the phenylvinyl or phenylallyl radicals, it being understood that in these radicals the phenyl radical can be replaced just as well by a naphthyl, pyridyl radical or also for example one of the aryl radicals as defined above; as examples of such arylalkynyl radicals, there can be mentioned for example the phenyl- ethynyl radical.

As examples of alkyl radicals substituted by an aryl radical, there can be mentioned, for example, the arylalkyl radicals defined above.

As examples of alkenyl radicals substituted by an aryl radical, there can be mentioned, for example, the arylalkenyl radicals as defined above.

The term aryloxy radical preferably designates the radicals in which the aryl radical is as defined above such as for example in phenoxy, the term arylalkoxy radical preferably designates the radicals in which the aryl radical and the alkoxy radical represent the radicals as defined above such as for example in benzyloxy, phenylethoxy or phenylisopropoxy, the term arylthio radical preferably designates the radicals in which the aryl radical represents the radicals as defined above such as for example in phenylthio, pyridylthio or pyrimidylthio, imidazolylthio or N-methylimidazolylthio, the term alkylthio radical preferably designates the radicals in which the alkyl radical is as defined above such as for example in methylthio, ethylthio, propylthio, isopropylthio, butylthio, sec-butylthio, tert-butylthio, isopentylthio or isohexylthio, optionally substituted as for example in hydroxymethylthio or aminoethylthio, the term haloalkylthio radical preferably designates the radicals in which the alkyl radical is as defined above and is substituted by one or more halogen atoms as defined above such as for example in bromoethylthio, trifluoromethylthio, trifluoroethylthio or also pentafluoroethylthio, the term arylalkylthio or alkylthio radical substituted by aryl represents for example the benzylthio or phenethylthio radical.

In all the radicals which can be represented by or carried by $R_1$, $R_2$, $R_3$ and $R_4$, as defined above, the sulphur atoms can be non-oxidized as in alkylthio, arylthio, cycloalkylthio radicals such as for example cyclohexylthio or on the other hand be oxidized to give the alkylsulphinyl, cycloalkylsulphinyl, arylsulphinyl, alkylsulphonyl, cycloalkylsulphonyl or arylsulphonyl radicals:

the terms alkylsulphinyl and alkylsulphonyl radical designate the alkylthio radicals in which the linear or branched alkyl radical can represent, for example, the values indicated above for the alkyl radical and in which the thio radical is oxidized into the sulphinyl or sulphonyl radical. For example, the methylsulphinyl, ethylsulphinyl, methylsulphonyl or ethylsulphonyl radicals can be mentioned, the term arylsulphinyl and arylsulphonyl radical designates the arylthio radicals, in which the aryl radical can represent, for example, the values indicated above for the aryl radical and in which the thio radical is oxidized into the sulphinyl or sulphonyl radical such as for example in the following radicals: phenyl-sulphinyl or -sulphonyl, pyridyl-sulphinyl or -sulphonyl, or pyrimidyl-sulphinyl or -sulphonyl, imidazolyl-sulphinyl or -sulphonyl, or N-methylimidazolyl-sulphinyl or -sulphonyl.

The carbamoyl and amino radicals which can be represented by or carried by one or more of the optional substituents of the radicals defined in the products of formula (I) and in what follows, designate radicals in which to the nitrogen atom are linked two identical or different radicals, chosen from the hydrogen atom to give the amino radical; alkyl radicals as defined above to give monoalkyl- or dialkylamino radicals in which the linear or branched alkyl radicals contain 1 to 6 carbon atoms, all these radicals being optionally substituted as indicated above and hereafter.

The carbocyclic or heterocyclic radicals which can be represented by $R_6$, $R_7$, $R_8$ and $R_9$ can take the values defined above for these radicals and in particular phenyl, benzyl, phenethyl, naphthyl, indolyl, indolinyl, thienyl, furyl, pyrrolyl, pyridyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl.

When $R_6$ and $R_7$ on the one hand, $R_8$ and $R_9$ on the other hand or $R_{14}$ and $R_{15}$ also on the other hand, as defined above, form together with the nitrogen atom to which they are linked, a heterocycle, it is, for example, one of the following rings: pyrrolyl, imidazolyl, indolyl, indolinyl, purinyl, pyrrolidinyl, piperidino, morpholino, piperazinyl, imidazolidinyl, pyrazolidinyl, thiomorpholinyl, azepine; these radicals can be optionally substituted by one or more radicals as defined previously and in particular by one or more radicals chosen from chlorine and fluorine atoms, the following radicals: methyl, ethyl, isopropyl, tert-butyl, methoxy, ethoxy, propoxy, benzoyl, methoxycarbonyl, ethoxycarbonyl, such as for example in methylpiperazinyl, fluoromethylpiperazinyl, ethylpiperazinyl, propylpiperazinyl, phenylpiperazinyl or benzylpiperazinyl: in these last two radicals, the phenyl and benzyl radicals can be substituted as indicated previously in the aryl, arylalkyl and arylalkenyl radicals, such as for example in chlorophenyl or trifluorophenyl.

The heterocycle which can be formed by $R_6$ and $R_7$ on the one hand, $R_8$ and $R_9$ on the other hand, respectively with the nitrogen atom to which they are linked, preferably represents a saturated heterocycle.

Similarly, in the products of formula (I), the carbamoyl or amino radicals are such that the radicals carried by the nitrogen atom, are identical or different, can represent aliphatic or cyclized chains or can form with the nitrogen atom to which they are linked a heterocycle, as has been defined above for $R_6$, $R_7$, $R_8$, $R_9$.

The optionally substituted amino and optionally substituted carbamoyl radicals designate respectively the radicals in which one or both hydrogen atoms linked to the nitrogen atom can be substituted by one or two radicals chosen from the radicals as defined previously.

The optionally substituted amino radical thus designates the amino radical optionally substituted by one or two alkyl radicals chosen from the alkyl radicals as defined above such as for example monoalkylamino in methylamino or ethylamino or isopropylamino or for example dialkylamino in dimethylamino, diethylamino or also methylethylamino, these alkyl radicals being optionally substituted as indicated above, such as for example the methoxymethyl, methoxyethyl, ethoxyethyl radicals.

By way of example and in a non-exhaustive manner, the term optionally substituted carbamoyl radical designates the carbamoyl radicals optionally substituted on the nitrogen atom by one or two alkyl radicals optionally substituted as defined above, in order to form in particular an N-monoalkyl carbamoyl group such as N-methylcarbamoyl, N-ethylcarbamoyl or an N,N-dialkyl carbamoyl group, such as N,N-dimethylcarbamoyl, N,N-diethylcarbamoyl; an N-(hydroxyalkyl) carbamoyl group, such as N-(hydroxymethyl) carbamoyl, N-(hydroxyethyl) carbamoyl, phenylcarbamoyl; pyridylcarbamoyl; benzylcarbamoyl; N-methyl N-phenylcarbamoyl; pyridylmethylcarbamoyl. Furthermore, among the substituted alkyl radicals, there can also be mentioned the alkyl radicals substituted by a carbamoyl radical as defined above, in order to form a carbamoylalkyl group such as carbamoylmethyl or carbamoylethyl.

The amino radical can be an alkoxycarbonylamino radical, this radical then preferably being the tert-butyl-oxycarbonyl-amino radical or the benzyloxycarbonylamino radical.

The amino and carbamoyl radicals can also in particular be substituted by one or two amino acids 5 natural amino 20 natural amino acids such as in particular proline or for example glycine, alanine, leucine, isoleucine, valine or phenylalanine or one of the other natural amino acids known to a man skilled in the art.

According to whether m1 represents the value 0, 1, 2, 3 or 4, the —$(CH_2)_{m1}$— radical represents a single bond, the methylene radical, the ethylene, propylene, isopropylene or butylene radical.

The carboxy radical or radicals of the products of formula (I) can be salified or esterified by the various groups known to a man skilled in the art amongst which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine, among the esterification compounds, the alkyl radicals to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, hydroxyl, alkoxy, acyl, acyloxy, alkylthio, amino or aryl radicals as, for example, in the chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, aryl-monosulphonic such as benzenesulphonic and aryldisulfonic.

When $R_2$ and $R_3$ both represent a sulphur group, $R_2$ and $R_3$ being identical or different, in the preferred products of the invention, these sulphur groups do not necessarily have the same oxidation number.

A particular subject of the invention is the use as defined above, of the products of formula (I) and corresponding to formula $(I_A)$:

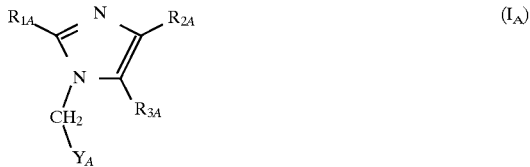

in which:

$R_{1A}$ represents a hydroxyl, alkyl, alkenyl, alkynyl, alkoxy, alkylthio radical, each of these radicals being linear or branched and containing at most 12 carbon atoms, a formyl radical or a cycloalkyl radical containing 3 to 7 carbon atoms or a dioxolane or dioxane radical, all these radicals being optionally substituted by one or more identical or different radicals chosen from halogen atoms, hydroxyl, alkoxy and alkylthio radicals, containing at most 6 carbon atoms, acyl, free, salified, esterified or amidified carboxy, cyano, nitro radicals, amino radicals optionally substituted by one or two identical or different alkyl radicals containing at most 6 carbon atoms, cycloalkyl radicals containing 3 to 7 carbon atoms and phenyl radicals optionally substituted by one or more radicals chosen from halogen atoms, hydroxyl radicals, alkyl and alkoxy radicals containing at most 4 carbon atoms, trifluoromethyl, free, salified or esterified carboxy, cyano and tetrazolyl radicals, $R_{2A}$ and $R_{3A}$, identical or different, are chosen from:

a) halogen atoms, mercapto, acyl, free, salified or esterified carboxy or carboxycarbonyl, nitro, cyano radicals, b) the $R_{4A}$ and $-OR_{4A}$ radicals in which:

either $R_{4A}$ represents the $(CH_2)_{m3}-S(O)_{m2}-XA-R_{10A}$ radical in which m3 represents the values 0 and 1, m2 represents the values 0 to 2 and either $-X_A-R_{10A}$ represents the amino radical or $X_A$ represents a single bond or the $-NH$, $-NHCO-$, $-NH-CO-O-$, $-NH-CO-NH-$ and $-N=CH-NR_{11A}$ radicals with $R_{10A}$ representing an alkyl, alkenyl or aryl radical, these radicals being optionally substituted by one or more substituents chosen from halogen atoms; hydroxyl radicals, alkyl and alkoxy radicals containing at most 4 carbon atoms; trifluoromethyl radicals; nitro radicals; cyclohexyl radicals; cyclopentyl radicals; aryl radicals optionally substituted by one or more identical or different radicals chosen from halogen atoms, hydroxyl radicals, alkyl and alkoxy radicals containing at most 6 carbon atoms, trifluoromethyl, free, salified or esterified carboxy, cyano, nitro radicals, amino radicals optionally substituted by one or two identical or different alkyl radicals containing at most 4 carbon atoms, and $R_{11A}$ represents the hydrogen atom or the values defined for $R_{10A}$, or $R_{4A}$ represents a hydrogen atom, an alkyl, alkenyl and acyl radical, these radicals being linear or branched and containing at most 6 carbon atoms, and being optionally interrupted by one or more heteroatoms chosen from sulphur, oxygen or nitrogen atoms, an amino radical optionally substituted by one or two identical or different alkyl radicals containing at most 6 carbon atoms, a cycloalkyl radical containing 3 to 6 carbon atoms or an aryl radical, the alkyl, alkenyl and aryl radicals of all the radicals which are represented by $R_4$, being optionally substituted by one or more identical or different radicals chosen from:

halogen atoms, hydroxyl, mercapto, cyano, azido, nitro, $SO_3H$, free, salified, esterified or amidified carboxy radicals, alkyl, alkenyl, alkoxy, haloalkyl, alkylthio, acyl, acyloxy, acylthio, haloalkylthio, haloalkoxy radicals, these radicals containing at most 6 carbon atoms, aryl, arylalkyl, arylalkenyl, arylthio, aryloxy and arylalkoxy radicals in which the aryl radical is optionally substituted by one or more identical or different radicals chosen from halogen atoms, hydroxyl, alkyl and alkoxy radicals containing at most 6 carbon atoms, trifluoromethyl, free, salified or esterified carboxy, cyano, nitro radicals, amino radicals optionally substituted by one or two identical or different alkyl radicals containing at most 4 carbon atoms, tetrazolyl radicals and phenyl radicals optionally substituted by one or more radicals chosen from halogen atoms, hydroxyl radicals, alkyl and alkoxy radicals containing at most 4 carbon atoms, trifluoromethyl and free, salified or esterified carboxy radicals,

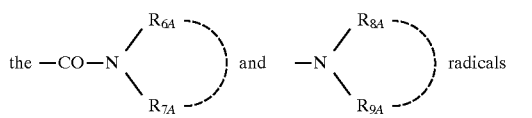

in which:

either $R_{6A}$ and $R_{7A}$ or $R_{8A}$ and $R_{9A}$ identical or different, are chosen from:

the hydrogen atom, alkyl radicals containing at most 4 carbon atoms and optionally substituted by one or more identical or different radicals chosen from halogen atoms, the hydroxyl radical or alkoxy radicals containing at most 4 carbon atoms, aryl and arylalkyl radicals in which the linear or branched alkyl radicals contain at most 4 carbon atoms, these aryl and arylalkyl radicals being optionally substituted by one or more radicals chosen from halogen atoms, hydroxyl, nitro, cyano, trifluoromethyl radicals, the alkyl, alkoxy and acyl radicals containing at most 6 carbon atoms, amino radicals optionally substituted by one or two identical or different alkyl radicals containing at most 4 carbon atoms, free, salified or esterified carboxy, tetrazolyl and phenyl radicals, optionally substituted by one or more radicals chosen from halogen atoms, hydroxyl, trifluoromethyl, nitro, cyano, free, salified or esterified carboxy and tetrazolyl radicals, or $R_{6A}$ and $R_{7A}$ or $R_{8A}$ and $R_{9A}$ form respectively with the nitrogen atom to which they are linked a monocyclic radical containing 5, 6 or 7 members or a radical constituted by condensed rings containing 8 to 14 members, these identical or different radicals optionally containing one or more other heteroatoms chosen from oxygen, nitrogen and sulphur atoms, and being optionally substituted by one or more radicals chosen from halogen atoms, hydroxyl, nitro, cyano, trifluoromethyl radicals, the alkyl, alkoxy and acyl radicals containing at most 6 carbon atoms, amino radicals optionally substituted by one or two identical or different alkyl radicals containing at most 4 carbon atoms, free, salified, esterified or amidified carboxy, tetrazolyl, oxazolyl and phenyl radicals, optionally substituted by one or more radicals chosen from halogen atoms, hydroxyl, trifluoromethyl, nitro, cyano, free, salified or esterified carboxy and tetrazolyl radicals, or $R_{8A}$ and $R_{9A}$, identical or different, represent an acyl radical or one of $R_{8A}$ or $R_{9A}$ represents a carbamoyl, alkoxycarbonyl or benzyloxycarbonyl radical and the other is chosen from the values defined above for $R_{8A}$ and $R_{9A}$ or $R_{8A}$ and $R_{9A}$ form together with the nitrogen atom to which they are linked a phthalimido or succinimido radical, $Y_A$ represents the $-Y_{1A}-B-Y_{2A}$ radical in which:

$Y_{1A}$ represents an aryl radical optionally substituted by one or more radicals chosen from the dioxol radicals and the radicals which can be represented by $R_{2A}$ and $R_{3A}$, B represents a single bond between $Y_{1A}$ and $Y_{2A}$ or one of the following divalent radicals: $-CO-$, $-O-$, $-NH-CO-$, $-CO-NH-$ or $-O-(CH_2)_p-$ with p representing the values 1, 2 or 3, $Y_{2A}$ is defined as follows:

either, whatever the value of B and $Y_{2A}$ being identical to or different from $Y_{1A}$, $Y_{2A}$ is chosen from the values defined for $Y_{1A}$, or, if B represents a single bond, $Y_{2A}$ represents a hydrogen atom, a halogen atom, a cyano radical, free, salified, esterified or amidified carboxy radical, a tetrazolyl radical or a $(CH_2)_{m3}-S(O)_{m2}-X_A-R_{10A}$ radical as defined above, said products of formula $(I_A)$ being in all the possible racemic, enantiomeric and diastereoisomeric isomer forms, as well as the addition salts with mineral and organic acids or with mineral and organic bases of said products of formula $(I_A)$.

A quite particular subject of the invention is the use as defined above, of the products of formula (I) and corresponding to formula (I$_B$):

in which:

R$_{1B}$ represents a linear or branched alkyl, alkoxy or alkylthio radical containing at most 6 carbon atoms, or a dioxolane or dioxane radical, all these radicals being optionally substituted by one or more identical or different radicals chosen from halogen atoms, hydroxyl radicals, alkoxy and alkylthio radicals, containing at most 6 carbon atoms, acyl, free, salified, esterified or amidified carboxy, cyano, nitro radicals, amino radicals optionally substituted by one or two identical or different alkyl radicals containing at most 6 carbon atoms, cycloalkyl radicals containing 3 to 7 carbon atoms and phenyl radicals optionally substituted by one or more radicals chosen from halogen atoms, hydroxyl radicals, alkyl and alkoxy radicals containing at most 4 carbon atoms, trifluoromethyl, free, salified or esterified carboxy, cyano and tetrazolyl radicals, R$_{2B}$ and R$_{3B}$, identical or different, are chosen from:
  a) halogen atoms; the mercapto radical; free, salified or esterified carboxy or carboxycarbonyl radicals; the hydroxyl radical; alkoxy and acyl radicals, containing at most 6 carbon atoms; cyano radicals; nitro radicals; benzoyl radicals;
  b) the R$_{4B}$ and —OR$_{4B}$ radicals, in which: either R$_{4B}$ represents the (CH$_2$)$_{m3}$—S(O)$_{m2}$—X$_B$—R$_{10B}$ in which m3 represents the values 0 and 1, m2 represents the values 0 to 2 and either —X$_B$—R$_{10B}$ represents the amino radical or X$_B$ represents a single bond or the —NH, —NHCO—, —NH—CO—O—, —NH—CO—NH— and —N=CH—NR$_{11B}$ radicals with R$_{10B}$ representing a methyl, ethyl, propyl, vinyl, allyl, pyridyl, phenyl, pyrimidinyl, tetrazolyl, thiazolyl, diazolyl, quinolyl or furyl radical, all these alkyl and alkenyl radicals being optionally substituted by one or more substituents chosen from halogen atoms, hydroxyl and alkoxy radicals containing at most 4 carbon atoms, trifluoromethyl, nitro, cyclohexyl, cyclopentyl, pyridyl, pyrimidinyl, thienyl, tetrazolyl and phenyl radicals, all the phenyl radical being optionally substituted by one or more radicals chosen from halogen atoms, hydroxyl radicals, alkoxy radicals containing at most 4 carbon atoms, cyano and tetrazolyl radicals, and R$_{11B}$ represents the hydrogen atom or the values defined for R$_{10B}$, or R$_{4B}$ represents a hydrogen atom or a linear or branched alkyl or alkenyl radical containing at most 6 carbon atoms, a cyclohexyl, phenyl, pyridyl, pyrimidinyl, tetrazolyl or imidazolyl radical, all these radicals being optionally substituted by one or more identical or different radicals chosen from:
  halogen atoms,
  hydroxyl, mercapto, acylthio, trifluoromethyl, trifluoromethylthio, trifluoromethoxy, cyano, azido, nitro, formyl, —SO$_3$H, free, salified, esterified or amidified carboxy radicals,
  alkyl, alkylthio, acyl, acyloxy and alkoxy radicals containing at most 6 carbon atoms, phenyl and phenylthio radicals, all these radicals themselves being optionally substituted by one or more radicals chosen from halogen atoms, the hydroxyl radical, alkoxy radicals containing at most 4 carbon atoms, free, salified, esterified or amidified carboxy, nitro and phenyl radicals,
  isoxazolyl, pyrrolidinyl, pyrrolidinylcarbonyl, pyridyl, pyrimidyl, thiazolyl, diazolyl, piperidinyl, tetrazolyl, tetrahydrofuranyl radicals, all these radicals being optionally substituted by a methyl, ethyl or nitro radical,

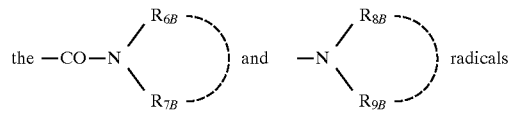

in which:

either R$_{6B}$, R$_{7B}$, R$_{8B}$ and R$_{9B}$, identical or different, are chosen from the hydrogen atom, alkyl radicals containing at most 4 carbon atoms and optionally substituted by one or more identical or different radicals chosen from halogen atoms, the hydroxyl radical or alkoxy radicals containing at most 4 carbon atoms, and phenyl, benzyl, phenethyl, azepine, piperidyl, morpholine, pyrrolidinyl, piperazinyl radicals, or on the one hand R$_{6B}$ and R$_{7B}$ and on the other hand R$_{8B}$ and R$_{9B}$ form respectively with the nitrogen atom to which they are linked a heterocyclic radical, these identical or different radicals being chosen from the following radicals: imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepine, indolyl, these radicals being optionally substituted by one or more identical or different radicals chosen from halogen atoms, hydroxyl radicals, nitro, cyano, acyl, trifluoromethyl, alkyl and alkoxy radicals, these radicals containing at most 4 carbon atoms, free, salified, esterified or amidified carboxy, tetrazolyl, oxazolyl and phenyl radicals, Y$_B$ represents the phenyl radical optionally substituted by one or more radicals chosen from halogen atoms, dioxol radicals, cyano radicals, free, salified or esterified carboxy radicals, the tetrazolyl radical and the —(CH(CH$_2$)$_{m3}$—S(O)$_{m2}$—X$_B$—R$_{10B}$ radical as defined above, said products of formula (I$_B$) being in all the possible racemic, enantiomeric and diastereoisomeric isomer forms, as well as the addition salts with mineral and organic acids or with mineral and organic bases of said products of formula (I$_B$).

The (CH$_2$)$_{m3}$—S(O)$_{m2}$—X$_B$—R$_{10B}$ radical can represent in particular the radicals in which X$_B$—R$_{10B}$ represents the following radicals:

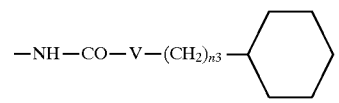

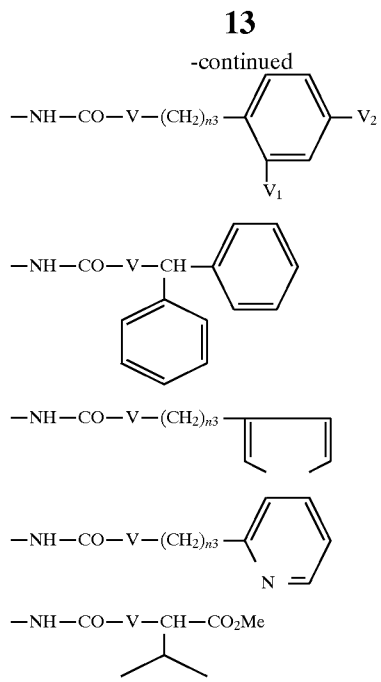

with n3 representing an integer from 0 to 3, V representing a single bond or the —NH— and —O— radicals, $V_1$ and $V_2$, identical or different, representing a hydrogen atom, a halogen atom, in particular chlorine or fluorine, and an alkoxy radical, in particular methoxy, and $V_4$ representing a hydrogen atom or an alkyl or alkenyl radical such as in particular methyl, ethyl, propyl, butyl, vinyl or allyl.

The $(CH_2)_{m3}$—$S(O)_{m2}$—$X_B$—$R_{10B}$ radical as defined above can thus represent for example and in a non-exhaustive manner, the following radicals:

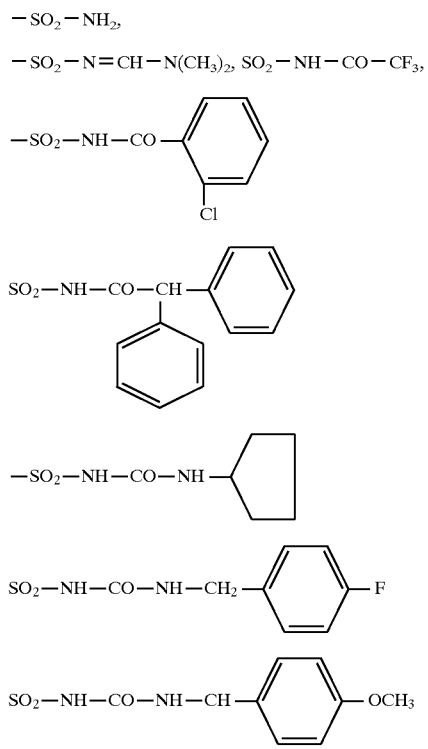

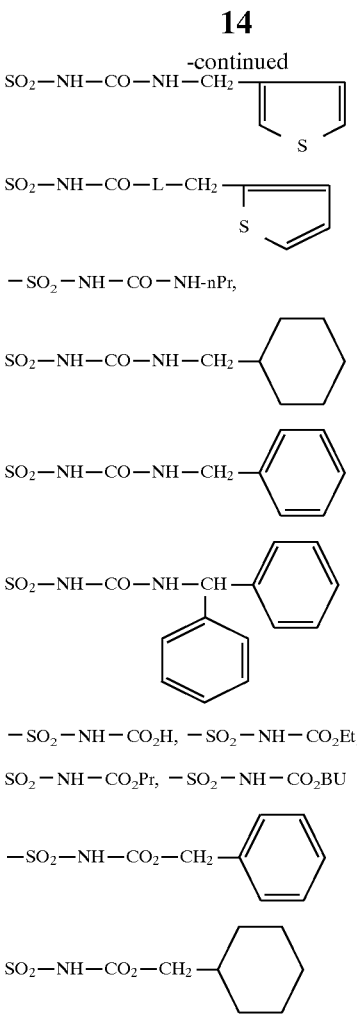

A more particular subject of the invention is the products of formula ($I_D$) corresponding to formula (I) as defined above, in which Y represents a benzofuranyl radical or a phenyl radical substituted by two radicals together forming a dioxol radical and optionally substituted by one or more substituents chosen from the values of $R_2$ and $R_3$, as defined above, said products of formula ($I_D$) being in all the possible racemic, enantiomeric and diastereoisomeric isomer forms, as well as the addition salts with mineral and organic acids or with mineral and organic bases of said products of formula ($I_D$).

A quite particular subject of the invention is the products of formula ($I_D$) as defined above and corresponding to formula ($I_C$):

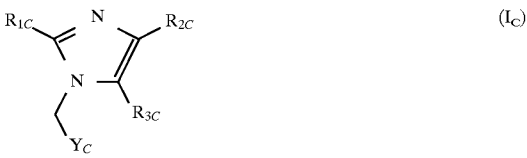

in which:
$R_{1C}$ represents a hydroxy, alkyl, alkoxy or alkylthio radical, linear or branched, containing at most 12 carbon atoms, a formyl radical or a dioxolane or dioxane radical, all these radicals being optionally substituted by one or more radicals chosen from hydroxyl radicals, free, salified, esterified or amidified carboxy radicals, linear or branched alkoxy radicals containing at most 4 carbon atoms and the phenyl radical itself optionally substituted by a hydroxyl or alkoxy radical, linear or branched, containing at most 4 carbon atoms, $R_{2C}$ and $R_{3C}$, identical or different, are chosen from:
a) halogen atoms; the carboxy or carboxycarbonyl radical, free, salified or esterified by an alkyl radical containing at most 4 carbon atoms; the formyl radical;
b) the $(CH_2)_{m3}$—$S(O)_{m2}$—$X_B$—$R_{10B}$ radical in which m3 represents the values 0 and 1, m2 represents the values 0 to 2 and either —$X_B$—$R_{10B}$ represents the amino radical or $X_B$ represents a single bond or the —NH, —NHCO—, —NH—CO—O—, —NH—CO—NH— and —N=CH—$NR_{11B}$ radicals with $R_{10B}$ representing a linear or branched alkyl or alkenyl radical containing at most 10 carbon atoms, the following radicals: pyridyl, phenyl, pyrimidinyl, tetrazolyl, thiazolyl, diazolyl, quinolyl or furyl, all these alkyl, alkenyl and phenyl radicals being optionally substituted by one or more substituents chosen from halogen atoms, hydroxyl radicals, alkyl, alkenyl and alkoxy radicals containing at most 4 carbon atoms, free, salified or esterified carboxy radicals, trifluoromethyl, nitro, cyclohexyl, cyclopentyl, pyridyl, pyrimidinyl, thienyl, tetrazolyl, morpholinyl and phenyl radicals, all the phenyl radicals being in addition optionally substituted by one or more radicals chosen from dioxole, cyano, tetrazolyl, alkyl and alkenyl radicals containing at most 4 carbon atoms, themselves optionally substituted by a carboxy radical, and $R_{11B}$ represents the hydrogen atom or the values defined for $R_{10B}$, and
c) alkyl, alkenyl radicals, containing at most 4 carbon atoms, the aryl, cycloalkyl or cycloalkenyl radical containing up to 6 carbon atoms and optionally one or more heteroatoms, these radicals being linked to the imidazole ring, either directly or by the Q substituent, Q representing an oxygen or sulphur atom, or a —$(CH_2)_{n'}$—, —$(CH_2)_{n'}$—S— radical, n' representing 1 to 4, —CH=CH—, —C≡C—,

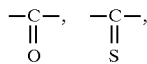

the sulphur atom being optionally oxidized in the form of the sulphoxide or sulphone, all these radicals being optionally substituted by one or more radicals chosen from halogen atoms, hydroxyl radicals, alkoxy radicals containing at most 4 carbon atoms, cycloalkyl, free salified or esterified carboxy, dioxol and phenyl radicals, the radicals being in addition optionally substituted by one or more radicals chosen from dioxole, alkyl, alkenyl radicals themselves optionally substituted by a free, salified or esterified carboxy radical and $Y_C$ represents the phenyl radical substituted by two radicals together forming a dioxol radical and optionally by one or more substituents chosen from the values of $R_{2C}$ and $R_{3C}$, said products of formula ($I_C$) being in all the possible racemic, enantiomeric and diastereoisomeric isomer forms, as well as the addition salts with mineral and organic acids or with mineral and organic bases of said products of formula ($I_C$).

In formula ($I_C$) defined above, by linear or branched alkyl or alkenyl radical which can be represented by $R_{10B}$, is meant in particular methyl, ethyl linear or branched, propyl, butyl, pentyl, hexyl, heptyl, octyl, vinyl, allyl radicals.

In formula ($I_C$) defined above, by aryl radical is meant in particular phenyl, morpholinyl or tetrazolyl.

Also a particular subject of the invention is the products of formula ($I_C$) as defined above, in which: $R_{IC}$ represents a linear or branched alkyl or alkoxy radical containing at most 4 carbon atoms, optionally substituted by one or more radicals chosen from the hydroxyl radical, alkoxy radical and the phenyl radical; a dioxolane radical; an alkylthio radical in which the linear or branched alkyl radical containing at most 12 carbon atoms is optionally substituted by a phenyl radical itself optionally substituted by one or more radicals chosen from halogen atoms and alkoxy radicals, and
a) $R_{2C}$ represents a halogen atom, a formyl radical, a linear or branched alkylthio or alkenylthio radical containing at most 8 carbon atoms optionally substituted by a hydroxy radical or a free, salified or esterified carboxy radical,
b) or $R_{2C}$ represents a cyclohexyl radical, a morpholinyl radical or a phenyl radical, all these radicals being linked to the imidazole ring either directly or by the Q substituent as defined above, the cyclohexyl and phenyl radicals being optionally substituted by one or more radicals chosen from halogen atoms, the following radicals: hydroxy and alkoxy, alkyl or alkenyl optionally substituted by a carboxy radical,
c) or $R_{2C}$ represents a

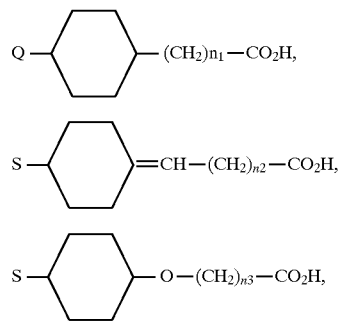

or also

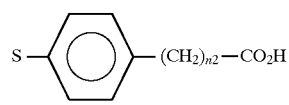

radical in which Q is as defined above, n1 represents a number comprised between 1 and 4, n2 represents a number comprised between 0 and 3 and n3 represents a number comprised between 1 and 3, $R_{3C}$ represents a free, esterified, salified or amidified carboxy radical, a sulphonylurea radical, a free or salified tetrazolyl radical or a linear or branched alkyl or alkenyl radical containing at most 4 carbon atoms optionally substituted by a free, esterified, salified or amidified carboxy radical, or a tetrazolyl or sulphonylurea radical, $Y_C$ represents a phenyl radical substituted by two radicals together forming a dioxol radical and optionally by one or more radicals chosen from halogen atoms, hydroxy, alkoxy, free, salified or esterified carboxy or carboxycarbonyl and tetrazolyl radicals, said products of formula ($I_C$) being in all the possible racemic, enantiomeric and diastereoisomeric isomer forms, as well as the addition salts with mineral and organic acids or with mineral and organic bases of said products of formula ($I_C$).

A more particular subject of the invention is the products of formula ($I_C$) as defined above, in which: $R_{1C}$ is chosen from linear or branched methyl, ethyl, propyl, butyl radicals optionally substituted by a hydroxy or alkoxy radical, and alkylthio radicals containing up to 6 carbon atoms, dioxolane and dioxane radicals, $R_{2C}$ is chosen from the following radicals:

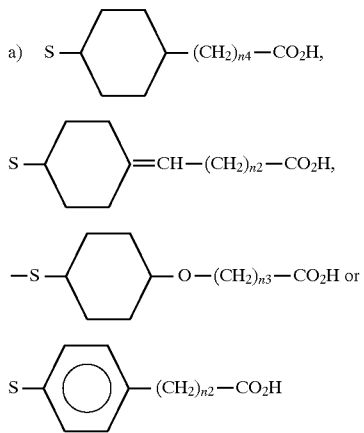

in which n4 represents the number 2 or 3 and n2 and n3 have the meaning indicated above, b) alkylthio, alkenylthio, cycloalkylthio, cycloalkyl, cycloalkylalkyl, cycloalkylalkenyl, phenyl, phenoxy, phenylthio, benzyl, benzoyl, phenylthioalkyl radicals, in which radicals the alkyl, alkenyl, cycloalkyl and phenyl radicals are optionally substituted by one or more radicals chosen from hydroxy, carboxy, alkyl, alkenyl and alkoxy radicals, these last three radicals themselves being optionally substituted by a carboxy radical and the phenyl radical more optionally being substituted on two adjacent carbons by a dioxole radical, $R_{3C}$ is chosen from free or esterified carboxy radicals, tetrazolyl or sulphonylurea radicals, $Y_C$ represents a phenyl radical substituted by two radicals together forming a dioxole radical and optionally by one or more radicals chosen from halogen atoms and hydroxy, alkoxy and carboxy radicals.

Among the products which are a subject of the invention, there can be mentioned quite particularly the products of formula ($I_C$) as defined above, corresponding to the following formulae:

1-((6-chloro 1,3-benzodioxol-5-yl)methyl)4-((4-methoxyphenyl)methylthio)1H-imidazole5-carboxylic acid, -2-butyl1-((6-chloro1,3-benzodioxol-5-yl)methyl)5-((4-methoxyphenyl)thio)1H-imidazole 4-carboxylic acid, -1-((6-chloro1,3-benzodioxol-5-yl)methyl)2,4-bis(((4-methoxyphenyl)methyl)thio)1H-imidazole5-carboxylic acid, 1-((6-chloro1,3-benzodioxol-5-yl)methyl)4-(4-(methoxyphenyl)thio)2-(propylthio) 1H-imidazole 5-carboxylic acid, 1-((6-chloro 1,3-benzodioxol-5-yl)methyl) 4-((3,4-dimethoxyphenyl)thio) 2-propyl1H-imidazole5-carboxylic acid, 2-butyl1-((6-chloro1,3-benzodioxol-5-yl)methyl)4-(cyclohexylthio)1H-imidazole5-carboxylic acid, 2-butyl4-((3-carboxypropyl)thio) 1-((6-chloro1,3-benzodioxol-5-yl)methyl)1H-imidazole5-carboxylic acid, 4-(((4-(2-carboxyethyl)phenyl)thio)methyl)1-((6-chloro1,3-benzodioxol-5-yl)methyl)2-propyl1H-imidazol5-carboxylic acid, 4-((3-carboxypropyl)thio)1-((6-chloro 1,3-benzodioxol-5-yl)methyl)2-propyl1H-imidazol5-carboxylic acid, -4-((7-carboxyheptyl)thio)1-((6-chloro1,3-benzodioxol-5-yl)methyl)2-propyl1H-imidazol5-carboxylic acid.

The products of formula (I) which do not correspond to formula ($I_D$) can be prepared in particular as indicated in the European Patent Applications EP 0465368 or EP 0503162.

The products of formula ($I_D$) and therefore the products of formula ($I_C$) can be prepared as follows.

Therefore a subject of the invention is also a preparation process for products of formula ($I_D$), as defined above, characterized in that: either a compound of formula (II):

in which $R'_1$ has the meaning indicated above for $R_1$, in which the optional reactive functions are optionally protected by protective groups, is subjected to a reaction with a compound of formula (III):

in which Hal represents a halogen atom, and Y' has the meaning indicated above for Y, in which the optional reactive functions are optionally protected by protective groups, in order to obtain the product of formula ($IV_1$):

in which $R'_1$ and Y' have the meanings indicated above, which product of formula ($IV_1$) can be subjected to a halogenation reaction, in order to obtain the product of formula ($IV_2$):

in which $R'_1$, Hal and Y' have the meanings indicated above, or a compound of formula (VIII):

in which Hal has the meaning indicated above, is subjected either to a reaction with the compound of formula (III) as defined above, or to the action of a protective group P, in order to obtain a product of formula (IX):

in which Hal has the meaning indicated above and W represents either —$CH_2$—Y' with Y' as defined above, or P which represents a protective group of the nitrogen atom, which product of formula (IX) is subjected to a halogen-metal exchange reaction then to a reaction with an electrophilic compound of formula (X), (X'), (XI), (XII) or (XII'):

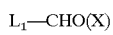   (X)

   (X')

   (XI)

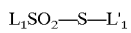   (XII)

   (XII')

in which $L_1$ and $L'_1$, identical or different, represent an alkyl, alkenyl or aryl radical, as defined above, in order to obtain a product of formula (XIII):

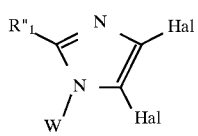   (XIII)

in which Hal and W have the meanings indicated above, $R''_1$ represents an aryl- or alkyl-carbonyl, aryl- or alkyl-hydroxyalkyl or alkylthio radical in which the aryl and alkyl radicals have the meanings indicated above and in which the optional reactive functions are optionally protected by protective groups, which products of formulae $(IV_2)$ and (XIII) can be subjected to a halogen-metal exchange reaction on one of the halogen atoms then to a reaction with $CO_2$ or DMF or an electrophilic compound of formula $(V_a)$, $(V_b)$, $(VI_a)$, $(VI_b)$ or $(VI_c)$:

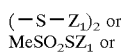   $(V_a)$
                       $(V_b)$

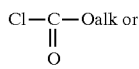   $(VI_a)$

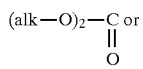   $(VI_b)$

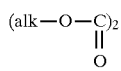   $(VI_c)$ in which $Z_1$ represents an optionally substituted alkyl, alkenyl or aryl radical, in which the optional reactive functions are optionally protected by protective groups, and alk represents an alkyl radical containing at most 4 carbon atoms, in order to obtain the compound of formula $(I_1)$:

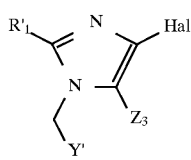   $(I_1)$ or the compound of formula (XIV):

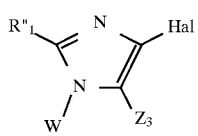   (XIV)

respectively, in which $R'_1$, $R''_1$, Hal, Y' and W have the meanings indicated above and $Z_3$ represents the carboxy radical, the formyl radical, the $S—Z_1$ radical as defined above, or the K—O-alk radical in which K represents the

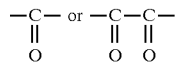

radical and alk has the meaning indicated above, which compounds of formula $(I_1)$ or (XIV), when $Z_3$ represents a formyl or esterified carboxy radical, can be subjected to a reaction with a compound of formula (VII):

   (VII)

in which S represents a sulphur atom, M represents a metal such as sodium, potassium or copper and $Z_2$ represents an optionally substituted alkyl, alkenyl or aryl radical, in which the optional reactive functions are optionally protected by protective groups in order to obtain the compound of formula $(I_2)$:

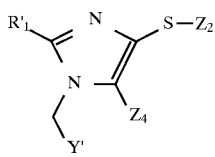   $(I_2)$ or the compound of formula (XV):

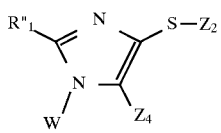   (XV)

respectively, in which $R'_1$, $R''_1$, Y', $Z_2$ and W have the meanings indicated above, and $Z_4$ represents the formyl or esterified carboxy radical, which products of formulae $(I_2)$ and (XV), when $Z_4$ represents the formyl radical, can be subjected to an oxidation or reduction reaction in order to obtain a product of formula $(I_3)$:

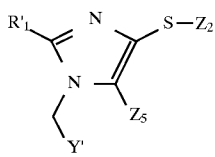   $(I_3)$ or a product of formula $(I_4)$:

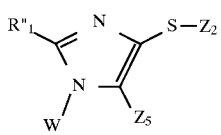   $(I_4)$ respectively, in which $R'_1$, $R''_1$, $Z_2$, Y' and W have the meanings indicated above, and $Z_5$ represents the $CH_2OH$ radical or the carboxy radical, which is free or esterified by a linear or branched alkyl radical containing at most 6 carbon atoms, which products of formula (XV) or $(I_4)$, in the case where W represents P as defined above and after release of the amine function blocked by P as defined above, is reacted with the compound of formula (III) as defined above, in order to obtain a product of formula $(I_5)$:

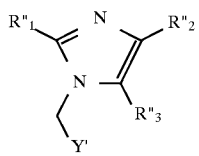

in which R"$_1$ and Y' have the meanings indicated above, and one of R"$_2$ and R"$_3$ represents indifferently $Z_4$ or $Z_5$ as defined above and the other represents S—$Z_2$, as defined above, or a compound of formula (XVI):

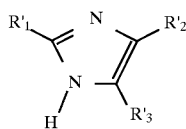

in which R'$_1$ has the meaning indicated above and R'$_2$ and R'$_3$ have the meanings indicated above for $R_2$ and $R_3$ respectively in which the optional reactive functions are optionally protected by protective groups, is subjected to a reaction with the compound of formula (III) as defined above, in order to obtain a product of formula (I'):

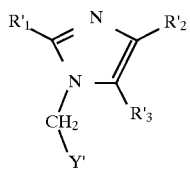

in which R'$_1$, R'$_2$, R'$_3$ and Y' have the definitions indicated above, or a compound of formula (XVII):

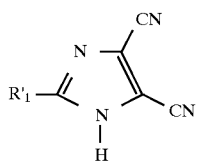

in which R'$_1$ has the meaning indicated previously, is subjected to an oxidation reaction in order to obtain the product of formula (XVIII):

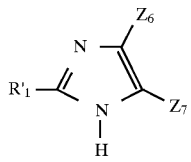

in which R'$_1$ has the meaning indicated previously and one or both of $Z_6$ and $Z_7$ represent a free or esterified carboxy radical and if appropriate, the other one of $Z_6$ and $Z_7$ retains the CN value, which product of formula (XVIII) is reacted with the compound of formula (III) as defined above in order to obtain the product of formula ($I_6$):

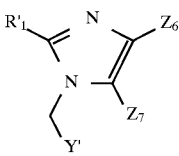

in which R'$_1$Y', $Z_6$ and $Z_7$ have the meanings indicated previously, which products of formulae ($I_1$), ($I_2$), ($I_3$), ($I_4$), (XIV), (XV), ($I_5$), ($I_6$) and (I') can be products of formula (I) and which, in order to obtain products or other products of formula (I), can be subjected, if desired and if necessary, to one or more of the following conversion reactions, in any order:

a) an esterification reaction of the acid function,
b) a saponification reaction of the ester function into an acid function,
c) a conversion reaction of the ester function into an acyl function,
d) a conversion reaction of the cyano function into an acid function,
e) a conversion reaction of the acid function into an amide function, then optionally into a thioamide function,
f) a reduction reaction of the carboxy function into an alcohol function,
g) a conversion reaction of the alkoxy function into a hydroxyl function, or also of the hydroxyl function into an alkoxy function,
h) an oxidation reaction of the alcohol function into an aldehyde, acid or ketone function,
i) a conversion reaction of the formyl radical into a carbamoyl radical,
j) a conversion reaction of the carbamoyl radical into a nitrile radical,
k) a conversion reaction of the nitrile radical into a tetrazolyl,
l) an oxidation reaction of the alkylthio or arylthio group into the corresponding sulphoxide or sulphone,
m) a conversion reaction of the sulphide, sulphoxide or sulphone function into the corresponding sulphoximine function,
n) a conversion reaction of the oxo function into a thioxo function,
o) a conversion reaction of the

radical into a

radical then if necessary again into a

radical with L1 as defined above,

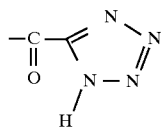

p) a conversion reaction of the acid function into the following function
q) a conversion reaction of the beta-keto-sulphoxide function into an alpha-keto thio ester function,
r) a conversion reaction of a carbamate into urea and in particular of a sulphonylcarbamate into sulphonylurea,
s) a conversion reaction of a halogenated function into a formyl or esterified carboxy function,
t) a conversion reaction of a formyl radical into a $CH_2$—$CO_2$alk or CH=CH—$CO_2$alk function in which alk represents an alkyl radical containing 1 to 4 carbon atoms, then if appropriate, conversion into the corresponding acid,
u) a conversion reaction of a formyl radical into a

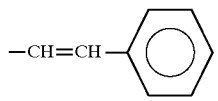

radical then if appropriate into a

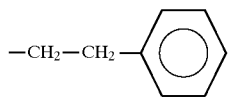

and

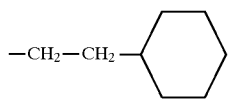

radical,
v) a conversion reaction of a formyl radical into a $CH_2$—OH or CH—OH radical then if appropriate into a $CH_2$—Rs radical Rs or conversion of CH—OH into C=O
|              |
Rs             Rs in order to obtain the optionally substituted alkyl or acyl radicals as defined above for $R'_2$ and $R'_3$,
w) an oxidation reaction of the S-alk radical into an

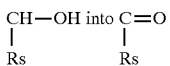

radical then conversion into an SH function and if appropriate into S—$Z_2$ in which alk and $Z_2$ have the meaning indicated previously,
x) an elimination reaction of the protective groups which can be carried by the protected reactive functions,
y) a salification reaction by a mineral or organic acid or by a base in order to obtain the corresponding salt, z) a resolution reaction of the racemic forms into resolved products,
said products of formula (I) thus obtained being in all the possible racemic, enantiomeric and diastereoisomeric isomer forms.

It can be noted that such conversion reactions of substituents into other substituents can also be carried out on the starting products as well as on the intermediate products as defined above before continuing the synthesis according to the reactions indicated in the process described above.

Under preferred conditions for implementing the invention, the process described above can be carried out in the following manner. In the product of formula (III), the halogen atom preferably represents a bromine atom but can also represent a chlorine or iodine atom. The condensation reaction of the imidazoles of formulae (II), (VIII), (XVI), (XV) and ($I_4$) as defined above (in the case of products of formulae (XV) and ($I_4$), when W represents P and after deprotection of the nitrogen atom), with the compound of formula (III) as defined above, in order to obtain respectively the products of formulae ($IV_1$), (IX) when W represents Y', ($I_5$) and (I') as defined above, can be carried out in a solvent such as for example dimethylformamide or also dimethylacetamide, tetrahydrofuran, dimethoxyethane or dimethylsulphoxide under reflux of the solvent or at ambient temperature, preferably under agitation; the reaction is preferably carried out in the presence of a base such as for example sodium or potassium hydride or also sodium or potassium carbonate, sodium or potassium methylate or ethylate or tert-butylate.

The halogenation reaction of the compound of formula ($IV_1$) as defined above into the compound of formula ($IV_2$) as defined above, can be carried out under the usual conditions known to a man skilled in the art and in particular by bromination using NBS in $CH_2Cl_2$ or also $Br_2$ in acetic acid.

The compounds of formulae ($IV_2$), (IX) and (XIII) as defined above can be subjected to a halogen-metal exchange reaction on the halogen atom by reaction with an organometallic compound such as nBuLi or EtMgBr in a solvent such as THF at a temperature of about −78° C. for BuLi and at ambient temperature for EtMgBr.

The carboxylation reaction using $CO_2$ and the formylation reaction using DMF of the compounds of formulae ($IV_2$) and (XIII) respectively into compounds of formulae ($I_1$) and (XIV) can be carried out according to the usual conditions known to a man skilled in the art, that being for example in tetrahydrofuran at ambient temperature.

$Z_1$ and $Z_2$, identical or different, represent an alkyl, alkenyl or aryl radical such that $Z_1$—S— and $Z_2$—S— represent the corresponding values defined above by $R_2$ and $R_3$ in which the optional reactive functions are optionally protected by protective groups.

$L_1$ and $L_1'$, identical or different, represent an alkyl, alkenyl or aryl radical such that $R_1''$ represents the corresponding values chosen from the values of $R_1$ as defined above in which the optional reactive functions are optionally protected by protective groups.

The reaction of the compound of formula ($IV_2$) or (XIII) as defined above with the compound of formula ($VI_a$), ($VI_b$) or ($VI_c$), as defined above, in order to obtain the corresponding compound of formula ($I_1$) or (XIV) respectively as defined above can be carried out in an identical manner using EtMgBr as metallation agent in tetrahydrofuran at ambient temperature.

The reaction of the compounds of formulae ($IV_2$) and (XIII) with the compounds of formula ($V_a$) or ($V_b$) can be carried out according to the usual conditions known to a man skilled in the art that being for example in tetrahydrofuran at ambient temperature.

The reaction of the compound of formula (IX) with the compounds of formulae (X), (XI), (XII) and (XII') can be carried out according to the usual conditions known to a man skilled in the art that being for example in tetrahydrofuran at ambient temperature.

The amine function of the compounds of formulae (XV) and (I$_4$) as defined above, protected by P as defined above, can be released under the usual conditions known to a man skilled in the art and in particular when P represents the —CH$_2$—O—(CH$_2$)$_2$—Si(CH$_3$)$_3$ radical, the hydrogen atom can be released in TFA or also in the presence of a fluoride ion.

The saponification reaction can be carried out according to the usual methods known to a man skilled in the art, such as for example in a solvent such as methanol or ethanol, dioxane or dimethoxyethane, in the presence of soda or potash or also caesium carbonate.

The reduction or oxidation reactions of the products of formulae (I$_2$) and (XV) respectively into products of formulae (I$_3$) and (I$_4$) can be carried out according to the usual methods known to a man skilled in the art.

According to the values of R'$_1$, R''$^1$, R'$_2$, R''$_2$, R'$_3$, R''$_3$, the products of formulae (I$_1$), (I$_2$), (I$_3$), (I$_4$), (I$_5$), (I$_6$), (XIV), (IV$_2$), (XV) and (I') constitute or do not constitute products of formula (I) and can give products of formula (I), or be converted into other products of formula (I) by being subjected to one or more of reactions a) to z) indicated above.

Thus the various reactive functions which can be carried by certain compounds of the reactions defined above can, if necessary, be protected: they are for example the hydroxyl, acyl, free carboxy or also amino and monoalkylamino radicals which can be protected by the appropriate protective groups.

The following non-exhaustive list of examples of the protection of reactive functions can be mentioned:
- the hydroxyl groups can be protected for example by alkyl radicals such as tert-butyl, trimethylsilyl, tert-butyl-dimethylsilyl, methoxymethyl, tetrahydropyrannyl, benzyl or acetyl,
- the amino groups can be protected for example by the acetyl, trityl, benzyl, tert-butoxycarbonyl, phthalimido radicals or other radicals known in the chemistry of the peptides,
- the acyl groups such as the formyl group can be protected for example in the form of cyclic or non-cyclic ketals or thioketals such as dimethyl- or diethylketal or ethylenedioxyketal, or diethylthioketal or ethylenedithioketal,
- the acid functions of the products described above can be, if desired, amidified by a primary or secondary amine for example in methylene chloride in the presence, for example, of 1-ethyl-3-(dimethylaminopropyl) carbodiimide hydrochloride at ambient temperature:
- the acid functions can be protected for example in the form of esters formed with easily cleavable esters such as benzyl or terbutyl esters or esters known in the chemistry of the peptides.

The reactions to which the products of formulae (I$_1$), (I$_2$), (I$_3$), (I$_4$), (I$_5$), (IV$_2$), (XIV), (XV) and (I'), as defined above, can be subjected, if desired or if necessary, can be carried out, for example, as indicated hereafter.

a) The products described above can, if desired, be subjected, on the optional carboxy functions, to esterification reactions which can be carried out according to the usual methods known to a man skilled in the art.

b) The optional conversions of ester functions into an acid function of the products described above can, if desired, be carried out under the usual conditions known to a man skilled in the art, in particular by acid or alkaline hydrolysis for example using soda or potash in an alcoholic medium such as, for example, in methanol or also using sulphuric or hydrochloric acid.

c) The addition reaction on the

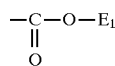

ester function in which E$_1$ can represent an alkyl or aryl radical optionally, substituted and optionally protected as the

acyl function can be carried out in particular by the action of the carbonated anion

in which E$_2$, E$_3$ and E$_4$, identical or different, are chosen from the hydrogen atom, the following radicals: alkyl, alkylthioaryl, alkylsulphoxide, arylsulphoxide, alkylsulphone, arylsulphone, acyl, free, salified, esterified or amidified carboxy, the alkyl, alkylthio and aryl radicals being optionally substituted and optionally protected as indicated above.

Such a reaction is carried out in particular as described in the experimental part, or according to the usual methods known to a man skilled in the art.

d) The optional cyano functions of the products described above can, if desired, be converted into an acid function under the usual conditions known to a man skilled in the art for example by a double hydrolysis carried out in an acid medium such as for example in a mixture of sulphuric acid, glacial acetic acid and water, these three compounds preferably being in equal proportions, or also in a mixture of soda, ethanol and water under reflux.

e) The conversion reaction of the acid function into an amide function can in particular be carried out by formation, first of all, of an acid chloride according to the usual conditions known to a man skilled in the art and for example by the action of SOCl$_2$ then amidification as above, or also by direct amidification of the above acid.

In particular the following radical can be obtained

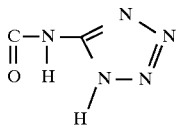

by converting the acid function into an acid chloride, in particular by the action of SOCl$_2$ in a solvent such as for example toluene, or benzene, then by reacting the amine

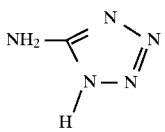

The amide thus obtained can then, if desired, be converted into a thioamide by the action in particular of a LAWESSON reagent in toluene.

f) The optional free or esterified carboxy functions of the products described above can, if desired, be reduced to an alcohol function by methods known to a man skilled in the art: the optional esterified carboxy functions can, if desired, be reduced to an alcohol function by the methods known to a man skilled in the art and in particular by lithium and aluminium hydride in a solvent such as for example tetrahydrofuran or also dioxane or ethyl ether.

The optional free carboxy functions of the products described above can, if desired, be reduced to an alcohol function in particular by boron hydride.

g) The optional alkoxy functions, such as in particular methoxy, of the products described above can, if desired, be converted into a hydroxyl function under the usual conditions known to a man skilled in the art for example using boron tribromide in a solvent such as for example methylene chloride, using pyridine hydrobromide or hydrochloride or also using hydrobromic or hydrochloric acid in water or trifluoroacetic acid under reflux.

h) The optional alcohol functions of the products described above can, if desired, be converted into an aldehyde or acid function by oxidation under the usual conditions known to a man skilled in the art such as for example by the action of manganese oxide in order to obtain the aldehydes or of a Jones reagent in order to obtain the acids.

i) j) The conversion reactions of the formyl radical into a carbamoyl radical and of the carbamoyl radical into a nitrile radical, are carried out in particular for $R_3$ and $R_4$ according to the usual conditions known to a man skilled in the art, such as for example passage through keto nitrile and displacement by an amine (Chem. Comm. 1971, p. 733).

k) The optional nitrile functions of the products described above can, if desired, be converted into tetrazolyl under the usual conditions known to a man skilled in the art such as for example by the cycloaddition of a metal azide such as for example sodium azide or a trialkyltin azide on the nitrile function as indicated in the method described in the article referenced as follows:

J. Organometallic Chemistry., 33, 337 (1971) KOZIMA S. et al.

l) The optional alkylthio or arylthio groups of the products described above can, if desired, be converted into the corresponding sulphoxide or sulphone functions under the usual conditions known to a man skilled in the art such as for example using the peracid such as for example peracetic acid or metachloroperbenzoic acid or also using ozone, oxone, sodium periodate in a solvent such as for example methylene chloride or dioxane at ambient temperature.

The obtaining of the sulphoxide function can be favoured by an equimolar mixture of the product containing an alkylthio or arylthio group and the reagent such as in particular a peracid.

The obtaining of the sulphone function can be favoured by a mixture of the product containing an alkylthio or arylthio group with an excess of the reagent such as in particular a peracid.

m) The optional sulphide, sulphoxide or sulphone functions of the products described above can, if desired, be converted into the corresponding sulphoximine functions under the usual conditions known to a man skilled in the art: non-exhaustive examples of the preparation of products containing a sulphoximine function are described below.

Thus for example for the preparation of compounds such as the N-(arylsulphonyl) sulphoximines and for example in the case where the aryl group which is represented by X' is a toluene radical, the sulphoximine can be obtained by the action of paratoluenesulphonyl nitride on the corresponding sulphoxide, that is —S(O)CH$_3$ preferably in the presence of copper as indicated, for example, in the following reference:

J. A. C. S., 95, pp. 4287 (1973) JOHNSON C. R. et al.

Another method also used consists of treating N-tosylsulphilimine, itself prepared from the sulphide by the action, for example, of chloramine "T", with an oxidizing agent such as for example, sodium hypochlorite under phase transfer conditions as indicated, for example, in the following reference:

J. Org. Chem., 49, pp. 2282 (1984) AKUTAGAWA K. et al.

n) The conversion reaction of the oxo function into a thioxo function can be carried out in particular by a LAWESSON reagent under the conditions defined above.

o) The conversion reaction of the

radical into an

radical can in particular be carried out using an alcohol solvent such as for example manganese dioxide in dioxane.

The reverse conversion reaction of the

radical into an

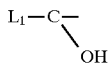

radical can in particular be carried out using sodium borohydride in ethanol.

p) The conversion reaction of the acid function into a tetrazolylcarboxy function can be carried out for example by preliminary conversion of the acid function into an acid chloride as indicated above, then by the action of Cu—C≡N, according to the usual conditions known to a man skilled in the art, on the acid chloride thus obtained, in this way the

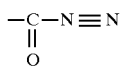

radical is obtained which can be converted into the following radical

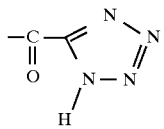

for example by the action of the compound Sn(Bu)₃N₃ in toluene, q) the conversion reaction of the beta keto sulphoxide function into an alpha keto thioester function, can be carried out by bromination in the alpha position of the ketosulphoxide for example by the action of NBS in for example methylene chloride then by a PUMMERER reaction carried out in a mixture of trifluoroacetic acid and methylene chloride or also a mixture of sulphuric acid and dioxane.

In particular, as defined above in c) and q), the following reaction diagram can be implemented:

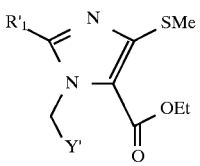
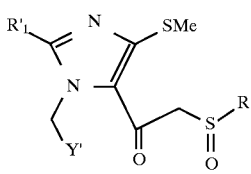
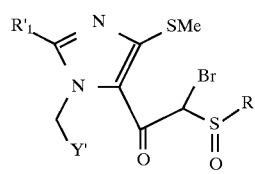

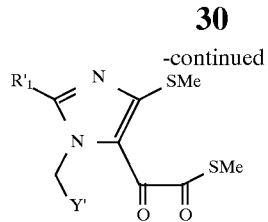

in which compounds R'₁ and Y' have the meanings indicated above, and R represents an alkyl or aryl radical optionally substituted as indicated above.

r) The conversion reaction of a carbamate into urea and in particular of a sulphonylcarbamate into sulphonylurea, can be carried out for example under reflux of a solvent such as for example toluene in the presence of an appropriate amine.

s) The conversion of a halogenated radical into a formyl radical can in particular be carried out by the action of an organo-metallic derivative, for example ethyl magnesium bromide, in an organic solvent, t) the conversion of the formyl radical into a CH=CH—CO₂alk radical can be carried out by a Wittig type reaction by condensation of an appropriate phosphonium salt in the presence of sodium hydride; the conversion into an acid is carried out by hydrolysis, for example using a base such as soda in an alcoholic medium, u) the conversion of the formyl radical into a

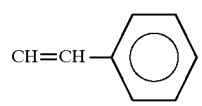

radical can be carried out by a Wittig reaction as indicated above; the conversion into a

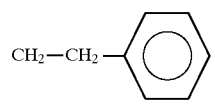 and 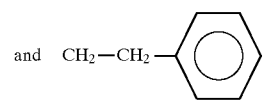

radical is carried out by reduction, using hydrogen in the presence of a catalyst, for example platinum oxide, v) the conversion of the formyl radical into a CH₂OH radical can be carried out using a reducing agent, for example sodium borohydride in ethanol at ambient temperature; the conversion into a CH₂Rs radical can be carried out by the action of the appropriate Rs-SH thiol on the intermediate mesylate prepared beforehand by the action of mesyl chloride on alcohol in the presence of Hunig's base, w) the oxidation of the S-alk substituent into sulphoxide can be carried out for example, by the action of metachloroperbenzoic acid; the conversion of the thiol is obtained by a PUMMERER reaction for example in the presence of trifluoroacetic anhydride; the conversion of the SH substituent into SZ₂ can be obtained by the action of a halogenated derivative Hal-Z₂ for example iodocyclohexane.

It is understood that the reactions described above can be carried out according to the usual methods known to a man skilled in the art.

x) The elimination of the protective groups such as for example those indicated above can be carried out under the usual conditions known to a man skilled in the art, in particular by acid hydrolysis carried out with an acid such as hydrochloric, benzene sulphonic or para-toluene sulphonic, formic or trifluoroacetic acid or also by catalytic hydrogenation.

The phthalimido group can be eliminated by hydrazine.

A list of the different protective groups which can be used will be found for example in the Patent BF 2,499,995.

y) The products described above can, if desired, be subjected to salification reactions, for example by a mineral or organic acid or by a mineral or organic base according to the usual methods known to a man skilled in the art.

z) The optional optically-active forms of the products described above can be prepared by resolution of the racemics according to the usual methods known to a man skilled in the art.

Illustrations of such reactions defined above are given in the preparation of the examples described hereafter.

The compounds of formula (I) as defied above as well as their addition salts with acids have useful pharmacological properties.

The products of formula (I) as defined above are endowed with antagonistic properties for the endothelin receptors and are thus in particular inhibitors of the effects of endothelin, in particular of the vaso-constrictive and hypertensive effects induced by endothelin. In particular an anti-ischemic effect is noted, the vaso-constrictive activity of endothelin being eliminated.

The products of formula (I) are also capable of opposing the stimulating effects of endothelin at the level of all cell types, in particular smooth muscle cells, neuronal cells and bone cells.

These properties justify their use in therapeutics and a particular subject of the invention is, as medicaments, the products of formula ($I_D$) corresponding to formul a (I) as defined above, in which Y contains at least one benzofuranyl radical or one phenyl radical substituted by a dioxol radical and optionally substituted by one or more substituents chosen from the values of $R_2$ and $R_3$, said products of formula ($I_D$) being in all the possible racemic, enantiomeric and diastereoisomeric isomer forms, as well as the addition salts with pharmaceutically acceptable mineral and organic acids or mineral and organic bases of said products of formula ($I_D$).

Therefore a subject of the invention is, as medicaments, the products as defined by formulae ($I_C$) and ($I_D$) above, said products of formulae ($I_C$) and ($I_D$) being in all the possible racemic or optically-active isomer forms, as well as the addition salts with pharmaceutically acceptable mineral and organic acid or mineral and organic bases of said products of formulae and ($I_D$).

A more particular subject of the invention is, as medicaments, the products of formula ($I_D$) as defined above and corresponding to formula ($I_C$):

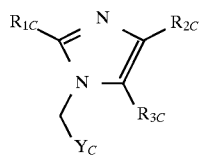

in which:

$R_{1C}$ represents a hydroxy, alkyl, alkoxy or alkylthio radical, linear or branched, containing at most 12 carbon atoms, a formyl radical or a dioxolane or dioxane radical, all these radicals being optionally substituted by one or more radicals chosen from hydroxyl, free, salified, esterified or amidified carboxy radicals, linear or branched alkoxy radicals containing at most 4 carbon atoms and the phenyl radical itself optionally substituted by a hydroxyl or alkoxy radical, linear or branched, containing at most 4 carbon atoms, $R_{2C}$ and $R_{3C}$, identical or different, are chosen from:

a) halogen atoms; the carboxy or carboxycarbonyl radical, free, salified or esterified by an alkyl radical containing at most 4 carbon atoms; the formyl radical;

b) the $(CH_2)_{m3}$—S(O)$_{m2}$—$X_B$—$R_{10B}$ radical in which m3 represents the values 0 and 1, m2 represents the values 0 to 2 and either —$X_B$—$R_{10B}$ represents the amino radical or $X_B$ represents a single bond or the —NH, —NHCO—, —NH—CO—O—, —NH—CO—NH— and —N=CH—NR$_{11B}$ radicals with $R_{10B}$ representing a linear or branched alkyl or alkenyl radical containing at most 10 carbon atoms, a pyridyl, phenyl, pyrimidinyl, tetrazolyl, thiazolyl, diazolyl, quinolyl or furyl radical, all these alkyl, alkenyl and phenyl radicals being optionally substituted by one or more substituents chosen from halogen atoms, hydroxyl, alkoxy radicals containing at most 4 carbon atoms, free, salified or esterified carboxy radicals, trifluoromethyl, nitro, cyclohexyl, cyclopentyl, pyridyl, pyrimidinyl, thienyl, tetrazolyl, morpholinyl and phenyl radicals, all the phenyl radicals being in addition optionally substituted by one or more radicals chosen from dioxole, cyano, tetrazolyl radicals, alkyl and alkenyl radicals containing at most 4 carbon atoms, themselves optionally substituted by a carboxy radical, and $R_{11B}$ represents the hydrogen atom or the values defined for $R_{10B}$, and c) alkyl, alkenyl radicals, containing at most 4 carbon atoms, the aryl or cycloalkyl radical containing up to 6 carbon atoms and optionally one or more heteroatoms, these radicals being linked to the imidazole ring, either directly or by the Q substituent, Q representing an oxygen or sulphur atom, or a —(CH$_2$)$_{n'}$—, —(CH$_2$)$_{n'}$—, —S— radical, n' representing 1 to 4, —CH=CH—, —C=C—,

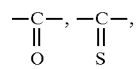

the sulphur atom being optionally oxidized in the form of the sulphoxide or sulphone, all these radicals being optionally substituted by one or more radicals chosen from halogen atoms, hydroxyl radicals, alkoxy radicals containing at most 4 carbon atoms, cycloalkyl, free salified or esterified carboxy, dioxol and phenyl radicals, the radicals being in addition optionally substituted by one or more radicals chosen from dioxole, alkyl, alkenyl radicals, themselves optionally substituted by a free, salified or esterified carboxy radical and $Y_C$ represents the phenyl radical substituted by two radicals together forming a dioxol radical and optionally by one or more substituents chosen from the values of $R_{2C}$ and $R_{3C}$, said products of formula ($I_C$) being in all the possible racemic, enantiomeric and diastereoisomeric isomer forms, as well as the addition salts with mineral and organic acids or with mineral and organic bases of said products of formula ($I_C$).

A more particular subject of the invention is, as medicaments, the products described hereafter in the examples and in particular the products of formula ($I_C$) as defined above, corresponding to the following formulae:

1-((6-chloro1,3-benzodioxol-5-yl)methyl)4-((4-methoxyphenyl)methylthio)1H-imidazole5-carboxylic acid, -2-butyl1-((6-chloro1,3-benzodioxol-5-yl)methyl)5-((4-methoxyphenyl)thio)1H-imidazole4-carboxylic acid, 1-((6-chloro1,3-benzodioxol-5-yl)methyl)2,4-bis(((4-methoxyphenyl)methyl)thio)1H-imidazole5-carboxylic acid, 1-((6-chloro1,3-benzodioxol-5-yl)methyl)4-(4-(methoxyphenyl)thio)2-(propylthio)1H-imidazole5-carboxylic acid, 1-((6-chloro1,3-benzodioxol-5-yl)methyl)4-((3,4-dimethoxyphenyl)thio)2-propyl1H-imidazole5-carboxylic acid, 2-butyl1-((6-chloro1,3-benzodioxol-5-yl)methyl)4-(cyclohexylthio)1H-imidazole5-carboxylic acid, 2-butyl4-((3-carboxypropyl)thio)1-((6-chloro1,3-benzodioxol-5-yl)methyl)1H-imidazole5-carboxylic acid, 4-(((4-(2-carboxyethyl)phenyl)thio)methyl)1-((6-chloro1,3-benzodioxol-5-yl)methyl)2-propyl1H-imidazol5-carboxylic acid, 4-((3-carboxypropyl)thio)1-((6-chloro1,3-benzodioxol-5-yl)methyl)2-propyl1H-imidazol5-carboxylic acid, 4-((7-carboxyheptyl)thio)1-((6-chloro1,3-benzodioxol-5-yl)methyl)2-propyl1H-imidazol5-carboxylic acid, as well as their addition salts with pharmaceutically acceptable mineral or organic acids or mineral and organic bases.

The medicaments, which are a subject of the invention, can be used, for example, in the treatment of all vascular spasms, in the treatment of post-cerebral haemorrhages, in the treatment of coronary spasms, peripheral vascular spasms as well as in the treatment of renal insufficiencies. These medicaments can also be used in the treatment of myocardial infarction, congestive cardiac insufficiency, in the prevention of post-angioplastic recurrence of stenosis, in the treatment of atherosclerosis, certain forms of hypertension such as in particular pulmonary hypertension, as well as in the treatment of asthma.

The medicaments, which are a subject of the invention, can also be used in the treatment of osteoporosis, prostatic hypertension and as neuronal protectors.

The invention extends to the pharmaceutical compositions containing as active ingredient at least one of the medicaments as defined above.

These pharmaceutical compositions can be administered by buccal, rectal route, by parenteral route or by local route as a topical application on the skin and mucous membranes or by injection by intravenous or intra-muscular route.

These compositions can be solid or liquid and can be presented in all the pharmaceutical forms commonly used in human medicine such as, for example, plain or sugar-coated tablets, capsules, granules, suppositories, injectable preparations, ointments, creams, gels and aerosol preparations; they are prepared according to usual the methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient being treated and the affection in question, can be, for example, from 1 to 300 mg per day for an adult, by oral route or from 1 to 100 mg per day by intravenous route.

Some of the starting products of formulae (II) and (XVI) are known and can be prepared for example as indicated in the European Patent EP 168,950.

Others starting products of formulae (II) and (XVI) can in particular be prepared as indicated in the European Patent EP 0,465,368, or also in the examples described hereafter in the experimental part, in particular in Examples 1 and 3.

Some of the starting products of formulae (II) and (XVI) are commercially available such as for example, the following products of formula (II):

2-methoxymethylimidazole 2-propylimidazole 2-isopropylimidazole 2-ethylimidazole 2-methylimidazole.

Examples of commercial products of formula (XVI) are given in the Patent EP 0,465,368 or EP 0,503,162.

Some of the products of formulae (II) and (XVI) can also in particular be prepared from products of formula (II) for example by subjecting them to one or more of the reactions described above in a) to z), carried out under the conditions also described above.

Some of the products of formula (XVI) can also be obtained by monohalogenation of the product of formula (II) as defined above into a product of formula ($P_1$):

in which $R'_1$ and P have the meanings indicated above for the product of formula (II), which product of formula ($P_1$) can be reacted, after exchange according to the halogen-metal reaction known to a man skilled in the art, with the appropriate electrophilic compound, according to the methods known to a man skilled in the art and in particular for example according to the same type of reaction described above for passing for example from the compound of formula (XIII) to the compound of formula (XIV).

Some of the products of formula (XVI) can also be prepared according to the following diagram:

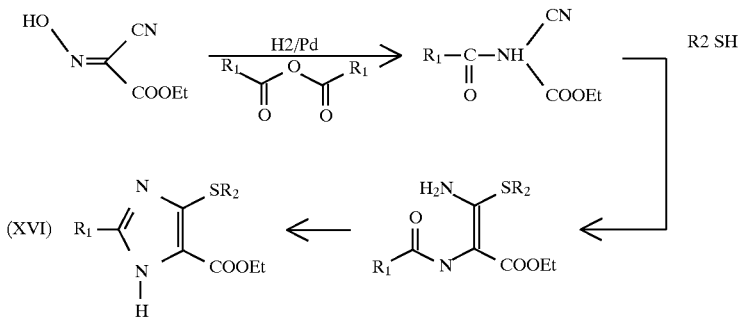

Some of the products of formula (XVI) can also be prepared according to the following diagram:

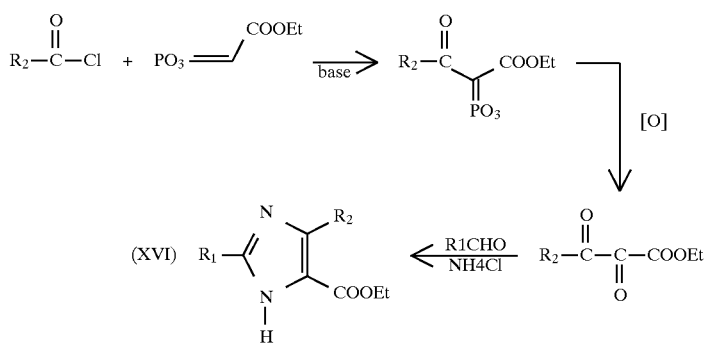

Some of the products of formula (XVI) can also be prepared according to the following diagram:

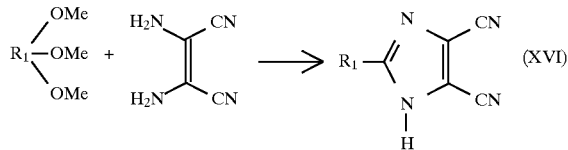

The starting compounds of formula (VIII) may be commercially available such as 2,4,5-tribromoimidazole or can be prepared according to the usual methods known to a man skilled in the art.

The starting products of formulae $(V_a)$, $(V_b)$, $(VI_a)$, $(VI_b)$ and $(VI_c)$, are commercial products such as in particular:

the following products of formula $(V_a)$ or (XI):
  sec-butyl disulphide
  ethyl disulphide
  isopropyl disulphide
  methyl disulphide
  benzyl disulphide
  phenyl disulphide
  propyl disulphide
the following products of formula $(V_b)$ or (XII):
  methyl methanethiosulphonate
  phenyl benzenethiol sulphonate
the following products of formula $(VI_C)$:
  methyl chloroformate
  benzyl chloroformate
  isobutyl chloroformate
  ethyl chloroformate
  N-propyl chloroformate the following products of formula $(VI_d)$:
  dimethyl carbonate
  diethyl carbonate
the following products of formula $(VI_e)$:
  di-tert-butyl oxalate
  diethyl oxalate
  dimethyl oxalate.

The starting products of formulae (X), (X') and (XII') are commercial products such as in particular:
  the following products of formula (X):
    benzaldehyde or butanal
  the following products of formula (X'):
    benzoyl or butyryl chloride
  the following products of formula (XII'):
    mesyl chloride
    tosyl chloride.

A preparation process of some of the products of formula (III) is in particular described in the European Patent EP 0,465,368.

Examples of the preparation of compounds of formula (III) are also described in the literature and such examples are given in particular in the U.S. Pat. No. 4,880,804 or for example in the reference Chemistry and Industry 7 Sep. 1987 HOWARD and COLQUHOUN pp. 612–617.

In particular, the product of formula (III) which is 6-chloro piperonyl chloride, is commercially-available from Janssen.

Finally a subject of the present invention is, as new industrial products, the compounds of formulae $(IV_1)$, $(IV_2)$, (XIII), (XIV) and (XV) in which Y' represents the phenyl radical substituted by a dioxol radical and optionally substituted by one or more substituents chosen from the values of $R_2$ and $R_3$, in which the optional reactive functions are optionally protected by protective groups.

Therefore a particular subject of the invention is the use of the products of formulae ($I_C$) and ($I_D$) as defined above, for the preparation of pharmaceutical compositions intended for the treatment of affections resulting from an abnormal stimulation of the endothelin receptors and in particular intended for the treatment of hypertension induced by endothelin, all vascular spasms, for the treatment of post-cerebral haemorrhages, renal insufficiencies, myocardial infarction and for the prevention of post-angioplastic recurrence of stenosis.

The following examples illustrate the invention without however limiting it.

EXAMPLE 1A ethyl 2-butyl-1-((6-chloro-1,3-benzodioxol-5-yl) methyl)-4-((4-methoxyphenyl)methylthio)-1H-imidazole-5-carboxylate

EXAMPLE 1B ethyl 2-butyl 1-((6-chloro-1,3-benzodioxol-5yl) methyl)-5-((4-methoxyphenyl)methylthio)-1H-imidazole-4-carboxylate

STAGE 1 ethyl((butylcarbonyl)amino)cyanoacetate 6.71 g of ethyl2-cyano-2-amino acetate (obtained as indicated in Chemistry and Industry 1980, 541–542 by F. I. Logemann G. Shaw) is introduced into 100 ml of methylene chloride. The solution is taken to 0° C. and 4.24 ml of pyridine, then 6.31 ml of acid chloride are added over 30 minutes at a temperature below 6° C.

Then the reaction medium is left to return to ambient temperature.

Toluene is added to eliminate the excess pyridine followed by taking up in 200 ml of methylene chloride and washing with water twice then drying.

The solid obtained is purified by impasting in isopropyl ether then filtration is carried out. In this way 8.40 g of expected product (white solid) is obtained, melting point 88° C.

Analyses

| NMR, H, ppm, CDCl$_3$ | |
|---|---|
| 0.93 (+) J = 7 | CH$_3$—CH$_2$—CH$_2$—CH$_2$ |
| 1.37 (m) | |
| 1.66 (m) | CH$_3$—(CH$_2$)$_2$ |
| 2.32 (m) | =C—CH$_2$—CH$_2$—CH$_2$—CH$_3$ |
| 1.37 (t) J = 7 | |
| 4.34 (m) | CO$_2$Et |
| 5.54 (d) J = 7.5 | CH—CO |
| 6.36 (wd) | NH—CO |

STAGE 2 ethyl 3-amino2-((butylcarbonyl)amino)3-(((4-methoxyphenyl)methyl)thio)propenoate 3 g of the product obtained in Stage 1 above, 4 ml of paramethoxybenzylmercaptan, 0.2 ml of triethylamine and 5 ml of ethanol are mixed together.

Agitation is carried out at ambient temperature for 3–4 days, the solvent is distilled off, the residue is taken up in isopropyl ether, the precipitate is filtered then washed abundantly with isopropyl ether. In this way 4.65 g of expected product (white solid) is obtained, M.p.=120° C.

Analyses

| IR CHCl$_3$ (cm$^{-1}$) | |
|---|---|
| =C—NH | 3488 |
| =C—NH$_2$ | 3458 |
|  | 3411 |
|  | 3360 |
| CO | 1665 complex |
| C=C | 1611 |
| aromatic | 1592 |
|  | 1513 |
| NH$_2$ | 1489 |

| Microanalysis | | |
|---|---|---|
|  | % calculated | % found |
| C | 58.99 | 58.90 |
| H | 7.15 | 7.17 |
| N | 7.64 | 7.63 |
| S | 8.75 | 8.79 |

STAGE 3 ethyl 2-butyl-4-((4-methoxyphenyl)-methylthio)-1H-imidazole-5-carboxylate

The operation is carried out starting with 1.14 g of phosphorus pentachloride in 20 ml of methylene chloride, the reaction medium is cooled down to 0° C. and 0.73 g of 4-dimethylamino pyridine in solution in 7 ml of methylene chloride is added. Next agitation is carried out for 5 minutes then 1 g of the product obtained in Stage 2 above in solution in 10 ml of methylene chloride is slowly added over about 5 minutes.

After chromatography on silica with EA/methylene chloride, 10:90, as eluant, 686 mg of expected product is obtained, M.p.=105° C.

Analyses

| IR CHCl$_3$ (cm$^{-1}$) | |
|---|---|
| =C—NH | 3435 |
| + | 3257 |
| >=O | max 1672 |
| Heterocycle | 1610 |
| + | 1582 |
| Aromatic | 1542 |
|  | 1513 |
|  | 1497 |
| OCH$_3$ | approx. 2836 |

STAGE 4 ethyl 2-butyl-1-((6-chloro-1,3-benzodioxol-5-yl) methyl)-4-((4-methoxyphenyl)methylthio)-1H-imidazole-5-carboxylate and ethyl2-butyl-1-((6-chloro-1,3-benzodioxol-5yl)methyl)-5-((4-methoxyphenyl)methylthio)-1H-imidazole-4-carboxylate 495 mg of the product obtained in Stage 3 above, 350 mg of 6-chloropiperonyl chloride and 235 mg of potassium bicarbonate are mixed with 14.2 ml of dimethylformamide, at ambient temperature, and the reaction medium is left for about 48 hours.

Hydrolysis is then carried out with $H_2O$ (ammonium chloride), followed by extraction with ethyl acetate and washing with $2 \times H_2O$ (ammonium chloride), $2 \times H_2O$, $2 \times H_2O$ (sodium chloride), drying, filtering and evaporating to dryness.

After purification on a silica column with ethyl acetate/cyclohexane (¼) as eluant, 557.6 mg of the expected product of Example 1A and 60.0 mg of the expected product of Example 1B are obtained.

Analyses

1) Example 1A

White solid

IR $CHCl_3$ ($cm^{-1}$)

absence of =C—NH

| | |
|---|---|
| >=0 | 1689 |
| aromatic + heteroaromatic | 1611 |
| | 1583 |
| | 1513 |
| | 1503 |

2) Example 1B

Oil

IR $CHCl_3$ ($cm^{-1}$)

absence of =C—NH

| | |
|---|---|
| >=0 | 1708 |
| heterocycle + aromatic | 1610 |
| | 1584 |
| | 1512 |
| | 1506 |
| | 1484 |

EXAMPLE 2

2-butyl-1-((6-chloro-1,3-benzodioxol-5yl) methyl)-4-((4-methoxyphenyl)methylthio)-1H-imidazole-5-carboxylic acid 536 mg of the product of Example 1A then 1.04 ml of 2N soda and 10 ml of tetrahydrofuran are put into 10.4 ml of ethanol and the whole is heated at 60° C. for 12 hours.

Then 10 ml of water (distilled) is added, evaporation under vacuum is carried out to eliminate the tetrahydrofuran and the ethanol, 20 ml of water (distilled) is added, this suspension is agitated thoroughly, 2.08 ml of hydrochloric acid (1N) is introduced dropwise then the reaction medium is left for one hour at ambient temperature under agitation, for 30 minutes under ultrasound and for one hour at 60° C. under agitation.

After cooling down to ambient temperature, filtration is carried out, followed by washing with distilled water (3×15 ml) and 460 mg of expected product (white solid) is obtained (M.p.=158° C.).

Analyses

| IR NUJOL >=0 1649 $cm^{-1}$ | |
|---|---|
| aromatic + heterocycle | 1615 |
| | 1589 |
| | 1514 |
| | 1502 |
| | 1482 |

| Microanalysis | | |
|---|---|---|
| | % calculated | % found |
| C | 58.95 | 58.9 |
| H | 5.15 | 5.2 |
| Cl | 7.25 | 7.5 |
| N | 5.72 | 5.6 |
| S | 6.55 | 6.8 |
| O | 16.35 | |

EXAMPLE 3A ethyl 2-butyl-1H-((6-chloro-1,3-benzodioxol-5-yl) methyl-4-((4-methoxyphenyl)thio)-1-imidazole-5-carboxylate

EXAMPLE 3B ethyl 2-butyl-1-((6-chloro-1,3-benzodioxol-5yl) methyl)-5-((4-methoxyphenyl)thio)-1H-imidazole-4-carboxylate

STAGE 1 ethyl 3-amino2-((butylcarbonyl)amino)3-((4-methoxyphenyl)thio)propenoate 1 g of the product obtained in Stage 1 of Example 1, 10 ml of 100% ethanol, 0.065 $cm^3$ of triethylamine and 1.72 ml of 4-methoxy thiophenol are mixed together.

Agitation is carried out at ambient temperature for 3 days. The reaction medium is taken to dryness, taken up in 10 ml of isopropyl ether, agitated for 30 minutes, separation is carried out followed by rinsing with isopropyl ether. 1.52 g of expected,product (white solid) is obtained (M.p.=122° C.).

Analyses

| Microanalysis | | |
|---|---|---|
| | % calculated | % found |
| C | 57.43 | 58.01 |
| H | 6.86 | 6.97 |
| N | 7.95 | 7.93 |
| S | 9.10 | 9.15 |

| IR Spectrum in $CHCl_3$ ($cm^{-1}$) | |
|---|---|
| =C—NH— | 3470 |
| =C—NH$_2$ | 3415 |
| | 3370 |
| | 3290 |
| >C=O | 1660 |
| NH$_2$ | 1593 |
| + Amide II | 1585 |
| + Aromatic | 1570 |
| + C=C | 1492 |

UV Spectrum in ethanol
  Max 235 nm=13900
  Max 290 nm=28800

STAGE 2 ethyl 2-butyl-4-((4-methoxyphenyl)thio)-1H-imidazole-5-carboxylate 1.75 g of phosphorus pentachloride and 87.5 ml of methylene chloride/NK$_{20}$ are mixed together and the mixture is cooled down to –70° C. then the solution of 1.127 g of 4-dimethylaminopyridine and 11.27 ml of methylene chloride/NK$_{20}$ is added over 5 minutes.

Agitation is carried out for 10 minutes at –70° C. then the solution of 1.48 g of the product obtained in Stage 1 above and 14.8 ml of methylene chloride/NK$_{20}$ is added over 5 minutes.

The reaction medium is left to return to ambient temperature and agitated for 16 hours. Hydrolysis is carried out by adding 100 ml of a saturated solution of sodium hydrocarbonate, followed by agitation for 30 minutes, decanting, re-extracting with 3×50 ml of methylene chloride, washing with 50 ml of water and drying. After chromatography on silica in methylene chloride—ethyl acetate (8/2), 1 g of expected product (cream solid) is isolated, M.p.=approx. 96° C.

Analyses

| Microanalysis | | |
|---|---|---|
| | % calculated | % found |
| C | 61.05 | 60.7 |
| H | 6.63 | 6.8 |
| N | 8.37 | 8.3 |
| S | 9.58 | 9.4 |
| IR in CHCl$_3$ (cm$^{-1}$) | | |
| =C—NH— + associated | 3433 | |
| complex C=O | 1688 | |
| Heterocycle | 1593 | |
| + | 1572 | |
| + Aromatic | 1543 | |
| | 1519 | |
| | 1494 | |
| UV Spectrum | | |
| In ethanol: | Infl 233 nm | ε = 13100 |
| (+ methylene chloride) | Max 251 nm | ε = 13800 |
| | Max 288 nm | ε = 8800 |
| | Infl 225 | |
| In ethanol—HCl (0.1N): | Max 242 nm | ε = 16200 |
| | Max 273 nm | ε = 8700 |
| | Infl 325 | |

STAGE 3 ethyl 2-butyl-1-((6-chloro-1,3-benzodioxol-5-yl)methyl-4-((4-methoxyphenyl)thio)-1H-imidazole-5-carboxylate and ethyl 2-butyl-1-((6-chloro-1,3-benzodioxol-5yl)methyl)-5-((4-methoxyphenyl)thio)-1H-imidazole-4-carboxylate The operation is carried out as in Example 1 starting with 1.6 g of the product obtained in Stage 2 above, 24 ml of dimethylformamide, 0.79 g of sodium bicarbonate and 1.14 g of 6-chloropiperonyl chloride which are left at ambient temperature for 48 hours.

After purification by chromatography on a silica column with methylene chloride—ethyl acetate 95–05 as eluant, 1.24 g of expected product of Example 3A (powder) (M.p.=100° C.) and 1.14 g of expected product of Example 3B (oil) are obtained.

Analyses

1) Example 3A

IR CHCl$_3$ (cm$^{-1}$)
Absence of =C—NH

| | |
|---|---|
| >=0 | 1691 |
| | 1627 |
| heterocycle | 1594 |
| + | 1575 |
| aromatics | 1505 |
| | 1494 |
| | 1483 |

2) Example 3B

IR CHCl$_3$ (cm$^{-1}$)
Absence of =C—NH

| | |
|---|---|
| >=0 | 1713 |
| | 1593 |
| heterocycle | 1575 |
| + | 1505 |
| aromatics | 1494 |

EXAMPLE 4

2-butyl-1-((6-chloro-1,3-benzodioxol-5-yl)methyl)-4-((4-methoxyphenyl)thio)-1H-imidazole-5-carboxylic acid The operation is carried out as in Example 2 starting with 0.35 g of the product of Example 3A, 3 ml of ethanol and 1 ml of methanol then 0.417 ml then 0.2 ml of 2N soda are introduced at ambient temperature.

The reaction medium is left for 14 hours at ambient temperature, brought to dryness, taken up in 10 ml of water then 0.62 ml of 2N hydrochloric acid.

In this way 290 mg of expected product is obtained (M.p.=186° C.).

Analyses
IR NUJOL (cm$^{-1}$)
General absorption OH/NH

| | |
|---|---|
| —C=0 | 1685 |
| | 1590 |
| heterocycle | 1570 |
| + | 1502 (F) |
| aromatic | 1490 (cp) |
| | 1480 (F) |

| UV Spectrum | |
|---|---|
| in ethanol | |
| max 232 nm | ε = 18100 |
| max 291 nm | ε = 16500 |

-continued

| in acetic acid—NaOH (N/10) | |
|---|---|
| max 241 nm | ε = 18900 |
| max 285 nm | ε = 11500 |

| Microanalysis | | |
|---|---|---|
| | % calculated | % found |
| C | 58.11 | 57.9 |
| H | 4.88 | 4.7 |
| N | 5.89 | 5.7 |
| S | 6.75 | 6.9 |
| Cl | 7.46 | 7.6 |

EXAMPLE 5 ethyl 2-butyl-1-((6-chloro-1,3-benzodioxol-5-yl)methyl)-4-((4-methoxyphenyl)sulphinyl-1H-imidazole-5-carboxylate 0.4 g of the product of Example 3A, 4 ml of methylene chloride/$NK_{20}$ and dropwise at 0° C. a solution of 0.174 g of metachloroperbenzoic acid at 85° C. in 1.7 cm$^3$ of methylene chloride/$NK_{20}$ are mixed together.

The mixture is left to rise to ambient temperature, left under agitation for 4 hours and then a further 0.03 g of metachloroperbenzoic acid in methylene chloride is added.

The reaction medium is left under agitation for 16 hours, then poured into 50 cm$^3$ of water, brought to pH 6–7 by the addition of 2 ml of a saturated sodium bicarbonate solution and extracted with 3×50 ml of methylene chloride.

The extracts are dried, filtered and brought to dryness.

After purification by chromatography on a silica column with methylene chloride—ethyl acetate 80–20 as eluant, 0.37 g of expected product (oil) is obtained.

Analyses

| IR CHCl$_3$ (cm$^{-1}$) | |
|---|---|
| >=0 | 1711 |
| heterocycle + aromatics | 1595, 1579, 1528, 1505, 1495 |

EXAMPLE 6

2-butyl-1-((6-chloro-1,3-benzodioxol-5-yl)methyl)-4-((4-methoxyphenyl)sulph-1H-imidazole-5-carboxylic acid The operation is carried out as in Example 2 starting with 350 mg of the product of Example 5 in 3.5 ml of ethanol. Next 0.438 ml of 2N soda is introduced and the reaction medium is left under agitation at ambient temperature for 4 hours. It is brought to dryness, the oily residue is taken up in 5 ml of water, filtration is carried out, 0.44 ml of 2N hydrochloric acid is added and the whole is left under agitation for half an hour. After filtration, washing with water and drying, 287 mg of expected product is obtained (M.p.=90° C.).

Analyses

| IR NUJOL (cm$^{-1}$): absorption region NH/OH | |
|---|---|
| >=0 | 1708 |
| heterocycle + aromatics | 1595, 1580, 1505, 1496 |
| S → 0 | 1035 |

| UV Spectrum | |
|---|---|
| in ethanol | |
| max 240 nm | ε = 21000 |
| inf 260, 280, 295 nm | |

| Microanalysis | | |
|---|---|---|
| | % calculated | % found |
| C | 56.26 | 55.9, 56.0 |
| H | 4.72 | 4.8, 4.6 |
| N | 5.70 | 5.6, 5.5 |
| S | 6.53 | 6.8 |
| Cl | 7.22 | 7.3 |

EXAMPLE 7

2-butyl-1-((6-chloro-1,3-benzodioxol-5-yl)methyl)-5-((4-methoxyphenyl)thio)-1H-imidazole-4-carboxylic acid The operation is carried out as in Example 2 starting with 0.250 g of the product of Example 3B in 2.5 ml of ethanol (10 vol).

0.35 ml of 2N soda is introduced and the whole is left under agitation for 14 hours, at ambient temperature.

The reaction medium is brought to dryness, the residue is taken up in 6 ml of water, then 0.35 ml of 2N hydrochloric acid is added under agitation.

In this way 207 mg of expected product is obtained (M.p.=82° C.).

Analyses

| IR in CHCl$_3$ (cm$^{-1}$) | |
|---|---|
| General absorption OH/NH | |
| >=0 | 1700 |
| heterocycle + aromatics | 1595, 1575, 1525, 1505, 1494 |

| Microanalysis | | |
|---|---|---|
| | % calculated | % found |
| C | 58.16 | 56.9, 57.8 |
| H | 4.88 | 4.9, 4.9 |
| N | 5.89 | 5.5, 5.8 |
| S | 6.75 | 6.5 |
| Cl | 7.46 | 7.6 |

EXAMPLE 8

2-butyl-1-((6-chloro-1,3-benzodioxol-5yl)methyl)-5-((4-methoxyphenyl)methylthio)-1H-imidazole carboxylic acid The operation is carried out as in Example 7 starting with the product of Example 1B and in this way the expected product is obtained.

EXAMPLE 9 ethyl 2-butyl-1-((6-chloro-1,3-benzodioxol-5-yl)
methyl)-4-((4-methoxyphenyl)sulphonyl)-1H-
imidazole-5-carboxylate 0.44 g of the product of Example 3A is introduced into 4.4 ml of methylene chloride and 0.397 g of metachloroperbenzoic acid at 85% and 2 ml of methylene chloride in solution are added dropwise at ambient temperature.

The reaction medium is left for 16 hours under agitation, at ambient temperature, poured into 50 ml of water, brought to a pH of about 6–7 by the addition of a saturated solution of sodium bicarbonate, extraction is carried out with 3 times 50 ml of methylene chloride, followed by drying, filtering and bringing to dryness.

After purification by chromatography on a silica column with methylene chloride—ethyl acetate 95:05 as eluant, 380 g of expected product is obtained.

Analyses

| IR Spectrum in CHCl$_3$ (cm$^{-1}$) | |
|---|---|
| >=0 | 1714 |
| —SO$_2$— | 1330 |
| | 1149 |
| Aromatics | 1597 |
| + | 1580 |
| heteroaromatics | 1506 |
| | 1499 |
| | 1485 |

EXAMPLE 10

2-butyl-1-((6-chloro-1,3-benzodioxol-5-yl)methyl)-
4-((4-methoxyphenyl)sulphonyl)-1H-imidazole-5-
carboxylic acid The operation is carried out as in Example 2 starting with 0.35 g of the product of Example 9, 3.5 ml of ethanol and 0.43 ml of 2N soda.

The reaction medium is left for 3 hours at ambient temperature under agitation, brought to dryness, the residue is taken up in 5 ml of water and 0.44 ml of 2N hydrochloric acid is added then the whole is left for 2 hours under agitation, followed by filtration and washing with water.

In this way 280 mg of expected product (powder) is obtained, M.p.=154° C.

Analyses

| IR in CHCl$_3$ (cm$^{-1}$) | |
|---|---|
| >=0 | 1730 |
| | 1598 |
| Aromatics | 1581 |
| + | 1507 |
| Heteroaromatics | 1500 |

| UV Spectrum | |
|---|---|
| in ethanol - hydrochloric acid N/10 | |
| max 245 nm | $\epsilon$ = 19800 |
| infl 257, 270, 279, 294 nm | |

| in ethanol - soda N/10 | |
|---|---|
| max 253 nm | $\epsilon$ = 19800 |
| max 292 nm | $\epsilon$ = 4200 |
| infl 270 nm | |

| Microanalysis | | |
|---|---|---|
| | % calculated | % found |
| C | 54.49 | 54.4 |
| H | 4.57 | 4.5 |
| N | 5.52 | 5.4 |
| S | 6.32 | 6.5 |
| Cl | 6.99 | 7.06 |

EXAMPLE 11

1-((6-chloro-1,3-benzodioxol-5-yl)methyl)-2,4-bis((
(4-methoxyphenyl)methyl)thio)-1H-imidazole-5-
carboxaldehyde

STAGE 1

1-((6-chloro-1,3-benzodioxol-5-yl)methyl)-2,4,5-
tribromo-1H-imidazole 25 g of 2,4,5-tribromoimidazole is introduced into 500 ml of dimethylformamide and 4.3 g of sodium hydride is added. Agitation is maintained for 10 minutes at ambient temperature. Next 18.4 g of 6-chloropiperonyl chloride is added to the reaction medium, then 25 g of sodium iodide is added and agitation is continued for 15 minutes at ambient temperature.

The reaction medium is finally poured into 3 litres of water, separation is carried out, followed by washing abundantly with water, then successively with 250 ml of ethanol, 250 ml of isopropanol, then finally with 250 ml of isopropyl ether.

After drying, 31.5 g of expected product (cream solid) is recovered, M.p.=225° C.

Analyses
IR CHCl$_3$ (cm$^{-1}$)
Absence of=C—NH
Aromatic heterocycle 1624–1506–1497–1485

STAGE 2

1-((6-chloro-1,3-benzodioxol-5-yl)methyl)-4,5-
dibromo-2-(phenylthio)-1H-imidazole 4.73 g of the product obtained above in Stage 1 is introduced into 100 ml of a methylene chloride/sulphuric ether mixture (20/80), to which is added dropwise 3.5 ml of ethyl magnesium bromide: the whole is maintained under agitation for 30 minutes at ambient temperature.

2.9 g of phenyl benzene thiosulphonate is then introduced into the reaction medium obtained. Agitation is maintained for 2 hours at ambient temperature.

The medium is hydrolyzed by the addition of dilute hydrochloric acid, after extraction with ethyl acetate, washing abundantly with water then drying, a cream solid is recovered which is purified by impasting in 50 ml of ethanol. In this way 3.35 g of the expected product is obtained, M.p. 165° C.

Analyses

| IR CHCl$_3$ (cm$^{-1}$) | |
|---|---|
| Heterocycle + aromatic | 1585-1508-1484 |

| Microanalysis | | |
|---|---|---|
| | % calculated | % found |
| C | 40.6 | 40.7 |
| H | 2.2 | 2.1 |
| N | 5.57 | 5.4 |
| S | 6.37 | 6.4 |
| Br | 31.8 | 31.4 |
| Cl | 7.05 | 6.8 |

STAGE 3

4-bromo-1-((6-chloro-1,3-benzodioxol-5-yl)methyl)-2-(phenylthio)-1H-imidazole-5-carboxaldehyde 6.4 g of the product obtained in Stage 2 above is introduced into 100 ml of tetrahydrofuran and 9.3 ml of ethyl magnesium bromide is added dropwise. The whole is maintained under agitation for 30 minutes at ambient temperature.

5 equivalents of dimethyl formamide are then introduced into the reaction medium obtained.

Agitation is maintained for 2 hours at ambient temperature.

The medium is hydrolyzed by the addition of dilute hydrochloric acid, after extraction with ethyl acetate, washing abundantly with water then drying, a brown solid is recovered which is purified by chromatography on silica with methylene chloride as eluant. 5 g of expected product is obtained (M.p.=155° C.) of which 500 mg is recrystallized from 25 ml of ethanol: after separating then drying 420 mg of expected product (white solid) is recovered (M.p.=155° C.).

Analyses

| IR CHCl$_3$ (cm$^{-1}$) | |
|---|---|
| C=0 | 1669 |
| Aromatic + Heteroatom | 1627-1580-1505-1485 |

| Microanalysis | | |
|---|---|---|
| | % calculated | % found |
| C | 47.9 | 47.9 |
| H | 2.67 | 2.6 |
| N | 6.2 | 6.1 |
| S | 7.09 | 7.2 |
| Br | 17.68 | 17.7 |
| Cl | 7.84 | 7.7 |

STAGE 4

1-((6-chloro-1,3-benzodioxol-5-yl)methyl)-2,4-bis((4-methoxyphenyl)methyl)thio)-1H-imidazole-5-carboxaldehyde 620 mg of sodium hydride at 50% in oil is introduced into 50 ml of tetrahydrofuran, to which 1.8 ml of methoxy-benzenemethanethiol is slowly added. Agitation is maintained for 15 minutes at ambient temperature.

A solution of 3.8 g of the product obtained in Stage 3 above in 25 ml of tetrahydrofuran is then added to the thiolate thus formed. Agitation is continued under these conditions for 2 hours 30 minutes.

The reaction medium is finally poured over 0.1N soda, after extraction with ethyl acetate, washing abundantly with water then drying, a brown resin is recovered which is purified by chromatography on silica with methylene chloride 80/cyclohexane 20, then methylene chloride +20% of ethyl acetate, as eluant.

2 fractions are collected, 1.98 g of the expected product B and 1.97 g of a second product A (M.p.=135° C.) which is formed under the same operating conditions: 1-((6-chloro-1,3-benzodioxol-5-yl)methyl)-4-(((4-methoxyphenyl)methyl) thio)-2-(phenylthio)-1H-imidazole-5-carboxaldehyde

ANALYSES FOR A

| IR CHCl$_3$ (cm$^{-1}$) | |
|---|---|
| C=O | 1660 |
| aromatic + Heterocycle | 1611-1580-1513-1505-1485 |

| Microanalysis | | |
|---|---|---|
| | % calculated | % found |
| C | 59.47 | 59.2 |
| H | 4.03 | 3.8 |
| N | 5.33 | 5.2 |
| S | 12.21 | 12.0 |
| Cl | 6.75 | 6.7 |

ANALYSES FOR B
IR CHCl$_3$ (cm$^{-1}$)
absence of phenyl S
C=O 1655
aromatic heterocycle 1612–1585–1512–1508–1485

EXAMPLE 12 methyl 1-((6-chloro-1,3-benzodioxol-5-yl)methyl)-2,4-bis(((4-methoxyphenyl)methyl)thio)-1H-imidazole-5-carboxylate A solution of 1 g of the product of Example 11 is introduced into a methylene chloride/methanol mixture (50 ml/100 ml), then 5 g of manganese oxide, 500 mg of sodium cyanide and 200 µl of acetic acid are successively added. Agitation is then maintained for 72 hours at ambient temperature.

Separation is carried out, followed by washing with methylene chloride, concentrating and purifying on silica with methylene chloride +20% of ethyl acetate as eluant.

In this way 750 mg of expected product (resin) is obtained.
Analyses
IR CHCl$_3$ (cm$^{-1}$)
ester 1696–1436
aromatic+heterocycle 1611–1585–1513–1505–1484

EXAMPLE 13

1-((6-chloro-1,3-benzodioxol-5-yl)methyl)-2,4-bis((4-methoxyphenyl)methyl)thio)-1H-imidazole-5-carboxylic acid The operation is carried out as in Example 2 starting with 580 mg of the product of Example 12 in an ethanol/tetrahydrofuran mixture (20 ml/60 ml) to which 20 ml of N soda is added.

Agitation is maintained for 48 hours at ambient temperature.

The reaction medium is acidified by the addition of 2N hydrochloric acid, extraction is carried out with ethyl acetate, the extracts are washed with water then dried and purified by chromatography on silica with methylene chloride+methanol as eluant.

Purification is carried out again by impasting in 50 ml of boiling ethanol, washing with 20 ml of ethyl acetate then drying and in this way 350 mg of expected product (white solid) is recovered, M.p.=210° C.

Analyses

| IR NUJOL (cm$^{-1}$) | |
|---|---|
| Complex absorption OH/NH | |
| —C=O | 1648 |
| Aromatic heteroatom | 1613-1585-1513-1502 |

| Microanalysis | | |
|---|---|---|
| | % calculated | % found |
| C | 57.47 | 57.3 |
| H | 4.3 | 4.2 |
| N | 4.79 | 4.7 |
| S | 10.96 | 10.7 |
| Cl | 6.06 | 6.4 |

EXAMPLE 14

4-bromo-1-((6-chloro-1,3-benzodioxol-5-yl)methyl)-2-(propylthio)-1H-imidazole-5-carboxaldehyde

STAGE 1

1-((6-chloro-1,3-benzodioxol-5-yl)methyl)-4,5-dibromo2-(propylthio)-1H-imidazole 5 g of the product obtained in Stage 1 of Example 11 is introduced into 100 ml of tetrahydrofuran.

This solution is cooled down to −78° C. then 7.8 ml of methyl lithium is slowly added to it. Agitation is maintained at this temperature for 10 minutes then 4 ml of dipropyl disulphide is added. Agitation is continued for 2 hours 30 minutes (ambient temperature).

The reaction medium is hydrolyzed by the addition of dilute soda, 100 ml of ethanol is added, followed by separating, washing abundantly with water then with 150 ml of ethanol.

In this way 1.8 g of expected product (cream solid) is obtained, M.p.=116° C.

Analyses
IR CHCl$_3$ (cm$^{-1}$)
Conjugated system 1627–1506–1484

STAGE 2

4-bromo-1-((6-chloro-1,3-benzodioxol-5-yl)methyl)-2-(propylthio)-1H-imidazole-5-carboxaldehyde 2.1 g of the product obtained in Stage 1 above is introduced into 30 ml of tetrahydrofuran and 10 ml of ethyl magnesium bromide is added dropwise. The reaction medium is maintained under agitation for 15 minutes at ambient temperature.

2 ml of dimethylformamide is then introduced into the reaction medium. Agitation is maintained for 2 hours at ambient temperature.

The medium is hydrolyzed by the addition of dilute hydrochloric acid, extraction is carried out with ethyl acetate, followed by washing with water then drying and purifying by impasting in 2×20 ml of ethanol.

In this way 1.4 g of expected product is obtained, M.p.=145° C.

Analyses

| IR CHCl$_3$ (cm$^{-1}$) | |
|---|---|
| C=O | 1663 |
| Aromatic + heterocycle | 1627-1505-1484 |

EXAMPLE 15

1-((6-chloro-1,3-benzodioxol-5-yl)methyl)-4-(4-methoxyphenyl)thio)-2-(propylthio)-1H-imidazole-5-carboxaldehyde 240 mg of sodium hydride at 50% in oil is introduced into 50 ml of tetrahydrofuran and 0.6 ml of paramethoxyphenylthiol is slowly added and agitation is maintained for 15 minutes at ambient temperature.

A solution of 1.4 g of the product of Example 14 in 20 ml of tetrahydrofuran is then introduced into the thiolate thus formed and agitation is carried out for 2 hours. The reaction medium is then poured over 0.1N soda, extraction is carried out with ethyl acetate, followed by washing with water, drying and purifying by chromatography on silica with methylene chloride as eluant. In this way 1.32 g of expected product is obtained.

Analyses

| IR CHCl$_3$ (cm$^{-1}$) | |
|---|---|
| C=O | 1657 |
| Aromatic + heterocycle | 1593-1570-1505-1494-1484- of which S-Φ-OCH$_3$ |

EXAMPLE 16 methyl 1-((6-chloro-1,3-benzodioxol-5-yl)methyl)-4-((4-methoxyphenyl)thio)-2-(propylthio)-1H-imidazole-5-carboxylate The operation is carried out as in Example 12 starting with 1.26 g of the product of Example 15 in a methylene chloride/methanol mixture (20 ml/100 ml) and 6 g of manganese oxide, 600 mg of sodium cyanide and 300 ul of acetic acid are successively added.

Agitation is then maintained for 24 hours at ambient temperature.

In this way 1.1 g of expected product is obtained.

Analyses

| IR CHCl$_3$ (cm$^{-1}$) | |
|---|---|
| ester | 1697-1436 |
| Aromatic + heterocycle | 1593-1575-1505-1494-1484 |

EXAMPLE 17

1-((6-chloro-1,3-benzodioxol-5-yl)methyl)-4-((4-methoxyphenyl)thio)-2-(propylthio)-1H-imidazole-5-carboxylic acid The operation is carried out as in Example 13 starting with 1 g of the product of Example 16 in an ethanol/tetrahydrofuran mixture (20 ml/20 ml) to which 25 ml of N soda is added.

Agitation is maintained for 48 hours at ambient temperature.

In this way 270 mg of expected product (white solid) is obtained, M.p.=164° C.

Analyses

| IR NUJOL (cm⁻¹) | |
|---|---|
| —C=O | 1650 |
| Aromatic heteroatom | 1592-1573-1508-1489 |

| Microanalysis | | |
|---|---|---|
| | % calculated | % found |
| C | 53.6 | 53.5 |
| H | 4.3 | 4.2 |
| N | 5.68 | 5.4 |
| S | 13.0 | 12.7 |
| Cl | 7.19 | 7.4 |

EXAMPLE 18

1-((6-chloro-1,3-benzodioxol-5-yl)methyl)-4-bromo2-methyl-1H-imidazole-5-carboxaldehyde

STAGE 1

1-((6-chloro-1,3-benzodioxol-5-yl)methyl)2-methyl-1H-imidazole

The operation is carried out as in Stage 1 of Example 11 starting with 12.3 g of 2-methyl-1H-imidazole, 7.92 g of sodium hydride with 50% oil, 150 ml of N dimethylformamide and 33.8 g of 6-chloropiperonyl chloride.

The expected product is obtained without being isolated.

STAGE 2

1-((6-chloro-1,3-benzodioxol-5-yl)methyl)-4,5-dibromo2-methyl-1H-imidazole

The crude product obtained in Stage 1 above is introduced into 58.7 g of N-bromosuccinimide and 200 ml of methylene chloride under reflux.

In this way 16.33 g of expected product is obtained, M.p.=185° C.

STAGE 3

1-((6-chloro-1,3-benzodioxol-5-yl)methyl)-4-bromo2-methyl-1H-imidazole-5-carboxaldehyde The operation is carried out as in Stage 3 of Example 11 starting with 15 g of the product obtained in Stage 2 above in 300 ml of tetrahydrofuran, 73.4 ml of ethyl magnesium bromide in solution in tetrahydrofuran and 28.4 ml of N-dimethylformamide.

In this way 9.8 g of expected product is obtained, M.p.=141° C.

EXAMPLE 19

1-((6-chloro-1,3-benzodioxol-5-yl)methyl)-4-((4-methoxyphenyl)thio)-2-methyl-1H-imidazole-5-carboxaldehyde The operation is carried out as in Stage 4 of Example 11 starting with 3 g of the product of Example 18, 765 mg of soda at 50% in oil and 1.96 ml of 4-methoxythiophenol in tetrahydrofuran.

In this way 3.08 g of (amorphous) expected product is obtained.

EXAMPLE 20 methyl 1-((6-chloro-1,3-benzodioxol-5-yl)methyl)-4-((4-methoxyphenyl)thio)-2-methyl-1H-imidazole-5-carboxylate The operation is carried out as in Example 12 starting with 1 g of the product of Example 19, 5 g of manganese oxide, 500 mg of sodium cyanide, 300 µl of acetic acid, 100 cm³ of methanol and 20 cm³ of methylene chloride.

In this way 410 mg of expected product is obtained, M.p.=152° C.

EXAMPLE 21

1-((6-chloro-1,3-benzodioxol-5-yl)methyl)-4-((4-methoxyphenyl)thio)-2-methyl-1H-imidazole-5-carboxylic acid The operation is carried out as in Example 13 starting with 740 mg of the product of Example 12, 25 ml of 1N soda and 25 ml of ethanol.

In this way 521 mg of expected product is obtained, M.p.=200°–210° C.

EXAMPLE 22

1-((6-chloro-1,3-benzodioxol-5-yl)methyl)-4-(((4-methoxyphenyl)methyl)thio)-2-methyl-1H-imidazole-5-carboxaldehyde The operation is carried out as in Stage 4 of Example 11 starting with 3 g of the product of Example 18, 564 mg of sodium hydride at 50% in oil and 1.63 ml of 4-methoxybenzylmercaptan in tetrahydrofuran.

In this way 1.28 g of (amorphous) expected product is obtained.

EXAMPLE 23 methyl 1-((6-chloro-1,3-benzodioxol-5-yl)methyl)-4-(((4-methoxyphenyl)methyl)thio)-2-methyl-1H-imidazole-5-carboxylate The operation is carried out as in Example 12 starting with 1.1 g of the product of Example 22, 7 g of manganese oxide, 700 mg of sodium cyanide, 400 µl of acetic acid, 100 ml of methanol and 20 ml of methylene chloride.

In this way 652 mg of expected product is obtained, M.p.=169° C.

EXAMPLE 24

1-((6-chloro-1,3-benzodioxol-5-yl)methyl)-4-(((4-methoxyphenyl)methyl)thio)-2-methyl-1H-imidazole-5-carboxylic acid The operation is carried out as in Example 13 starting with 489 mg of the product of Example 23, 25 ml of 1N soda, 25 ml of ethanol and 40 ml of tetrahydrofuran.

In this way 310 mg of expected product is obtained, M.p.=190° C.

EXAMPLE 25 methyl 2-benzoyl-1-((6-chloro-1,3-benzodioxol-5-yl)methyl)-4-((4-methoxyphenyl)thio)-1H-imidazole-5-carboxylate

STAGE 1

1-((6-chloro-1,3-benzodioxol-5-yl)methyl)-4,5-dibromo-alpha-phenyl-1H-imidazole-2-methanol 9.5 g of the product obtained in Stage 1 of Example 11 is introduced into a mixture of methylene chloride/sulphuric ether 100 ml/350 ml and 7.3 ml of ethyl magnesium bromide is added dropwise. The whole is maintained under agitation for 20 minutes at ambient temperature.

10 ml of benzaldehyde is then introduced into the reaction medium obtained.

Agitation is maintained for 2 hours at ambient temperature.

The medium is hydrolyzed by the addition of dilute hydrochloric acid, after extraction with ethyl acetate, washing abundantly with water then drying, a cream solid is recovered which is purified by impasting in 50 ml of ethanol.

In this way 5.34 g of expected product is obtained.
Analyses
IR $CHCl_3$ (cm$^{-1}$)
—OH 3603+general absorption
Aromatic heteroatom 1627–1603–1505–1484

STAGE 2

4-bromo-1-((6-chloro-1,3-benzodioxol-5-yl)methyl)-2-(alpha-hydroxy-(phenylmethyl))-1H-imidazole-5-carboxaldehyde 5.3 g of the product obtained in Stage 1 above is introduced into 100 ml of tetrahydrofuran and 11 ml of ethyl magnesium bromide is added dropwise. The mixture is maintained under agitation for 15 minutes at ambient temperature.

5 ml of dimethylformamide is then introduced into the reaction medium obtained. Agitation is maintained for 2 hours at ambient temperature.

The medium is hydrolyzed by the addition of dilute hydrochloric acid, after extraction with ethyl acetate, washing abundantly with water then drying, a brown solid is recovered which is purified by chromatography on silica with methylene chloride as eluant.

In this way 2.067 g of expected product is obtained.
Analyses

| IR $CHCl_3$ (cm$^{-1}$) | |
| --- | --- |
| C=O | 1674 |
| —OH | 3596 complex |
| Aromatic + heterocycle | 1628-1602-1505-1485 |

EXAMPLE 26

1-((6-chloro-1,3-benzodioxol-5-yl)methyl)-2-(alpha-hydroxy-(phenylmethyl))-4-((4-methoxyphenyl)thio)-1H-imidazole-5-carboxaldehyde The operation is carried out as in Example 13 starting with a suspension of 390 mg of sodium hydride at 50% in oil in 50 ml of tetrahydrofuran, to which 1 ml of methoxybenzenethiol is slowly added. Agitation is maintained for 15 minutes at ambient temperature.

A solution of 2.6 g of the product obtained in Example 25 in 25 ml of tetrahydrofuran is then introduced into the thiolate thus formed. Agitation is continued under these conditions for 2 hours.

In this way 2.15 g of expected product is obtained.

Analyses

| IR $CHCl_3$ (cm$^{-1}$) | |
| --- | --- |
| C=O | 1667 |
| —OH | 3598 associated |
| aromatic + heterocycle | 1593-1574-1505-1494-1484 |

EXAMPLE 27 methyl 1-((6-chloro-1,3-benzodioxol-5-yl)methyl)-2-(alpha-hydroxy-(phenylmethyl))-4-((4-methoxyphenyl)thio)-1H-imidazole-5-carboxylate

STAGE 1 methyl 2-benzoyl-1-((6-chloro-1,3-benzodioxol-5-yl)methyl)-4-((4-methoxyphenyl)thio)-1H-imidazole-5-carboxylate The operation is carried out as in Example 12 starting with 2.15 g of the product obtained in Example 26 in 200 ml of methanol, then 11 g of manganese oxide, 1.1 g of sodium cyanide and 700 µl of acetic acid are successively added. Agitation is then maintained for 48 hours at ambient temperature.

Proceeding as in Example 12, 1.32 g of expected product is obtained (M.p.=166° C.).
Analyses

| IR $CHCl_3$ (cm$^{-1}$) | |
| --- | --- |
| Absence of OH | |
| C=O | 1716-1653 |
| aromatic + heterocycle | 1597-1579-1508-1495 |

STAGE 2 methyl 1-((6-chloro-1,3-benzodioxol-5-yl) methyl)-2-(alpha-hydroxy-(phenylmethyl))-4-((4-methoxyphenyl)thio)-1H-imidazole-5-carboxylate 65 mg of sodium borohydride is added to a suspension of 820 mg of the product obtained in Stage 1 above in 200 ml of ethanol and the whole is left for 2 hours at ambient temperature. Ice is then added, the reaction medium is left for 30 minutes at ambient temperature then 200 ml of water is added, followed by filtration, washing with water and with ethanol and drying. In this way 770 mg of expected product is obtained, M.p.=193° C.

EXAMPLE 28

1-((6-chloro-1,3-benzodioxol-5-yl)methyl)-2-(alpha-hydroxy-(phenylmethyl))-4-((4-methoxyphenyl)thio)-1H-imidazole-5-carboxylic acid The operation is carried out as in Example 13 starting with 760 mg of the product of Example 27 in a mixture of acetic acid (50 ml) and tetrahydrofuran (50 ml) to which 20 ml of 1N soda is added and the whole is left for 48 hours at ambient temperature.

In this way 660 mg of expected product is obtained, M.p.=130° C.

EXAMPLE 29

1-((6-chloro 1,3-benzodioxol-5-yl)methyl)-4-((3,4-dimethoxyphenyl)thio-2-(1,3-dioxolan-2-yl)1H-imidazol-5-carboxaldehyde

STAGE A 1-((6-chloro1,3-benzodioxol-5-yl)methyl)4,5-dibromo2-(1,3-dioxolan-2-yl)1H-imidazole 15.6 ml of a 3M solution of ethyl magnesium bromide in ether is added to 20 g of product obtained as in Example 11

Stage A in 200 ml of dichloromethane and 500 ml of ether and the whole is agitated for 20 minutes at ambient temperature. 200 ml of N hydrochloric acid is added and extraction is carried out with ethyl acetate. The organic phase is washed with water, dried and the solvent is evaporated off. The intermediate aldehyde obtained is taken up in 200 ml of toluene, 20 ml of ethylene glycol is added and heating under reflux is carried out for 16 hours. The solvent is evaporated off, the residue is taken up in a saturated aqueous solution of sodium bicarbonate, extraction is carried out with ethyl acetate, followed by washing with water, drying, and the solvent is evaporated off under reduced pressure. The residue is impasted in isopropyl ether, followed by filtration and drying under reduced pressure and 13.5 g of expected product is collected. M.p.=188° C.

STAGE B 4-bromo1-((6-chloro1,3-benzodioxol-5-yl)methyl)2-(1,3-dioxolan-2-yl)1H-imidazol5-carboxaldehyde 10 g of the product obtained in Stage A above is introduced into 200 ml of tetrahydrofuran and 10 ml of ethyl magnesium bromide in a 3M solution in ether is added dropwise. The reaction medium is maintained under agitation for 20 minutes at ambient temperature. 10 ml of dimethylformamide is then added to the reaction medium obtained and agitation is carried out for 2 hours at ambient temperature. The medium is hydrolyzed by the addition of 200 ml of dilute hydrochloric acid, extraction is carried out with ethyl acetate, followed by washing with water then drying and after impasting in isopropyl ether, 7.6 g of expected product is recovered, which is used as it is for the following stage.

STAGE C 1-((6-chloro1,3-benzodioxol-5-yl)methyl)4-((3,4-dimethoxyphenyl)thio-2-(1,3-dioxolan-2-yl)1H-imidazol-5-carboxaldehyde 1.1 g of sodium hydride is added to 3.15 ml of 3,4-dimethoxythiophenol in solution in 200 ml of dimethylformamide and the whole is agitated for 20 minutes at ambient temperature. 7.6 g of the product obtained in Stage B is added, agitation is continued for 16 hours at ambient temperature, the solvent is evaporated under reduced pressure, the residue is taken up in 200 ml of a saturated aqueous solution of ammonium chloride and extraction is carried out with dichloromethane. The organic phase is dried, the solvent is evaporated off, the residue is impasted in isopropyl ether, filtration is carried out and 5.2 g of expected product is obtained. M.p.=149° C.

EXAMPLE 30 methyl 1-((6-chloro1,3-benzodioxol-5-yl)methyl)4-((3,4-dimethoxyphenyl)thio-2-(1,3-dioxolan-2-yl)1H-imidazol-5-carboxylate A solution of 5.05 g of the product of Example 29 is introduced into a mixture of methylene chloride/methanol (100 ml/500 ml), next 22 g of manganese oxide, 2.2 g of sodium cyanide and 1.5 ml of acetic acid are successively added then the whole is agitated for 72 hours at ambient temperature. After filtration, the organic phase is washed with water, dried, the solvent is evaporated off and after chromatography on silica 4.1 g of expected product is obtained. M.p.=170° C.

EXAMPLE 31

1-((6-chloro1,3-benzodioxol-5-yl)methyl)4-((3,4-dimethoxyphenyl)thio-2-(1,3-dioxolan-2-yl)1H-imidazol-5-carboxylic acid 1 g of the product obtained in Example 30 is introduced into 100 ml of ethanol and 50 ml of 2N soda is added. Agitation is carried out for 16 hours at ambient temperature, the solvent is evaporated off under reduced pressure, the residue is taken up in a mixture of ice-cooled water, acidified with 2N hydrochloric acid, extraction is carried out with ethyl acetate, followed by drying and the solvent is evaporated off under reduced pressure. 650 mg of expected product is recovered. M.p.=155° C.

By operating as in Examples 29 to 31 starting with the appropriate compounds, the products of the following examples were prepared:

EXAMPLE 32

1-((6-chloro1,3-benzodioxol-5-yl)methyl)4-((4-methoxyphenyl)thio-2-propyl)1H-imidazol-5-carboxylic acid M.p.=174.5° C.

EXAMPLE 33

1-((6-chloro1,3-benzodioxol-5-yl)methyl)4-((4-methoxyphenyl)thio)2-(1-methylethyl)1H-imidazol-5-carboxylic acid M.p.=179° C.

EXAMPLE 34

1-((6-chloro1,3-benzodioxol-5-yl)methyl) 4-((3,4-dimethoxyphenyl)thio)2-propyl)1H-imidazol-5-carboxylic acid M.p.=175° C.

EXAMPLE 35

4-(butylthio)1-((6-chloro1,3-benzodioxol-5-yl)methyl)2-propyl)1H-imidazol-5-carboxylic acid M.p.=151.8° C.

EXAMPLE 36

4-((2-carboxyphenyl)thio)1-((6-chloro1,3-benzodioxol-5-yl)methyl)2-(1-methylethyl)1H-imidazol-5-carboxylic acid M.p.=203° C.

EXAMPLE 37

1-((6-chloro1,3-benzodioxol-5-yl)methyl)2-(1-methylethyl)4-(phenylthio)1H-imidazol-5-carboxylic acid $R_f$=0.2 ($CH_2Cl_2$—$CH_3OH$ 95-5)

EXAMPLE 38

Potassium salt of 1-((6-chloro 1,3-benzodioxol-5-yl)methyl)4-((3,4-dimethoxyphenyl)thio)2-(1-hydroxy1-methylethyl)1H-imidazol-5-carboxylic acid The acid obtained as indicated above is dissolved in hot isopropanol then a solution of potash in isopropanol is added dropwise until a basic pH is obtained. After 4 hours of agitation at ambient temperature, the precipitate is separated off then washed with isopropanol and with isopropyl ether, dried and the expected product is obtained.

$R_f$=0.70 (AcOEt)

By operating as in Example 4 starting with the appropriate compounds, the products of the following examples were prepared:

EXAMPLE 39

2-butyl1-((6-chloro1,3-benzodioxol-5-yl)methyl)4-(methylthio)1H-imidazol-5-carboxylic acid M.p.=177° C.

EXAMPLE 40

1-((6-chloro1,3-benzodioxol-5-yl)methyl) 2-ethyl4-((4-methoxyphenyl)thio)1H-imidazol-5-carboxylic acid M.p.=172° C.

EXAMPLE 41

1-((6-chloro1,3-benzodioxol-5-yl)methyl) 4-(methylthio)2-propyl1H-imidazol-5-carboxylic acid M.p.=196° C.

EXAMPLE 42

4-((1,3-benzodioxol-5-yl)thio)1-((6-chloro1,3-benzodioxol-5-yl)methyl)2-propyl1H-imidazol-5-carboxylic acid M.p.=203° C.

EXAMPLE 43 ethyl 1-((6-chloro1,3-benzodioxol-5-yl)methyl)2-propyl1H-imidazol-4,5-dicarboxylate 2.54 g of ethyl 2-propyl 1H-imidazol 4,5-dicarboxylate prepared as indicated in Bio. Org. Med. Chem. Letters Vol. 4 No. 1 (177–182) 1994, is dissolved in 50 ml of dimethylformamide and 2.5 g of potassium carbonate, 2.5 g of 6-chloropiperonyl chloride then 2.5 g of sodium iodide are added. The suspension obtained is heated at 80° C. for one hour, the reaction medium is poured into ice-cooled water, extraction is carried out with ethyl acetate, followed by washing with water, drying, eliminating the solvent, the residue is chromatographed on silica (eluant: $CH_2Cl_2$-AcOEt 80-20) and 4.4 g of expected product is obtained.

$R_f$=0.36 ($CH_2Cl_2$-AcOEt 80-20).

EXAMPLE 44 ethyl 1-((6-chloro1,3-benzodioxol-5-yl)methyl)4-formyl2-propyl 1H-imidazol-5-carboxylate 3.3 g of the product obtained in Example 43 in 40 ml of tetrahydrofuran is cooled down to −78° C. and 6.5 ml of diisobutylaluminium hydride is added and the whole is agitated for 2 hours. The reaction medium is poured into a saturated aqueous solution of ammonium chloride, extraction is carried out with ethyl acetate, followed by washing with water, drying, the solvent is eliminated, the residue is chromatographed on silica (eluant: $CH_2Cl_2$-AcOEt 80-20) and 2.8 g of expected product is obtained. M.p.=105° C.

EXAMPLE 45 ethyl 1-((6-chloro1,3-benzodioxol-5-yl)methyl)4-(hydroxymethyl)2-propyl)1H-imidazol-5-carboxylate 2.1 g of the aldehyde obtained in Example 44 is dissolved in 100 ml of ethanol and 210 mg of sodium borohydride is added. Agitation is carried out for 15 minutes at ambient temperature, the excess reducing agent is destroyed by the addition of acetic acid, the solvent is eliminated under reduced pressure, the residue is taken up in water, alkalinization is carried out using ammonium hydroxide, the precipitate is separated off, washed with water, dried at 60° C. under reduced pressure and 1.88 g of expected product is obtained. M.p.=114° C.

EXAMPLE 46

1-((6-chloro1,3-benzodioxol-5-yl)methyl)4-(hydroxymethyl)2-propyl1H-imidazol-5-carboxylic acid 500 mg of the product obtained in Example 45 is dissolved in 25 ml of ethanol and 25 ml of soda. Agitation is carried out for 16 hours at ambient temperature, the solvent is eliminated under reduced pressure, the residue is taken up in water, followed by filtration, acidification by the addition of 2N hydrochloric acid, the precipitate is separated off, washed with water and with ethanol, dried under reduced pressure and 380 mg of expected product is obtained. M.p.=240° C.

By operating as in Example 46 starting with the aldehyde obtained in Example 44, the following product was obtained:

EXAMPLE 47

1-((6-chloro1,3-benzodioxol-5-yl)methyl) 4-formyl2-propyl1H-imidazol-5-carboxylic acid

EXAMPLE 48 ethyl 2-butyl1-((6-chloro1,3-benzodioxol-5-yl)methyl)4-(cyclohexylthio)1H-imidazol-5-carboxylate

STAGE A ethyl 2-butyl1-((6-chloro1,3-benzodioxol-2-yl)methyl)4-(methylsulphinyl)1H-imidazol5-carboxylate 10 g of the ethyl ester obtained starting from the product of Example 39 is dissolved in 500 ml of dichloromethane, the solution is cooled down to 0° C. and 6.6 g of metachloroperbenzoic acid is added followed by agitation for 2 hours 30 minutes. The reaction medium is washed with a sodium bicarbonate solution, extraction is carried out with dichloromethylene, the organic phase is washed with water, dried and the solvent is evaporated off under reduced pressure. 12 g of crude product is obtained which is chromatographed on silica (eluant: ethyl acetate—cyclohexane 7-3 then dichloromethane—methanol 85-15). 8.49 g of expected product is obtained. M.p.=103° C.

STAGE B ethyl 2-butyl1-((6-chloro1,3-benzodioxol-5-yl)methyl)4-mercapto1H-imidazol-5-carboxylate 1 g of the product obtained in Stage A is dissolved in 20 ml of dichloromethane and 0.66 ml of trifluoroacetic anhydride is added. Agitation is carried out for 30 minutes, the solvent is evaporated off under reduced pressure, the residue is taken up in 10 ml of methanol and 4 ml of triethylamine and agitation is continued for 30 minutes at ambient temperature, followed by extraction with chloroform, the organic phase is washed with a saturated aqueous solution of ammonium chloride, dried and the solvent is evaporated off under reduced pressure. The crude product is recrystallized from ether and 490 mg of expected product is collected. M.p.=114° C.

STAGE C ethyl 2-butyl1-((6-chloro1,3-benzodioxol-5-yl) methyl)4-(cyclohexylthio)1H-imidazol-5-carboxylate 125 mg of sodium hydride is added to a solution containing 950 mg of product obtained as in Stage B in 20 ml of dimethylformamide. Next 0.33 ml of iodocyclohexane is added and agitation is carried out for 3 hours at ambient temperature. 20 ml of a saturated aqueous solution of ammonium chloride is added, extraction is carried out with dichloromethane, followed by washing with water, drying and evaporating the solvent under reduced pressure. After chromatography on silica (eluant: $CH_2Cl_2$), 850 mg of expected product is obtained.

$R_f$=0.43 ($CH_2Cl_2$).

EXAMPLE 49

2-butyl1-((6-chloro1,3-benzodioxol-5-yl)methyl)4-(cyclohexylthio)1H-imidazol-5-carboxylic acid 800 mg of the product obtained in Example 48 is mixed with 50 ml of 2N soda and 50 ml of ethanol and tetrahydrofuran is added until complete dissolution is obtained. Agitation is carried out for 48 hours at ambient temperature, the organic solvents are evaporated off under reduced pressure, the solution is acidified to pH 1 using 2N hydrochloric acid, the precipitate formed is separated off, washed with water, dried at 40° C. under reduced pressure and 317 mg of expected product is recovered after recrystallization from methanol. M.p.=257° C.

By operating as in Example 49 starting with the appropriate compounds, the products of the following examples were prepared:

EXAMPLE 50

2-butyl 4-((2-carboxyethenyl)thio)1-((6-chloro1,3-benzodioxol-5-yl)methyl) 1H-imidazol-5-carboxylic acid M.p.=212° C.

EXAMPLE 51

2-butyl1-((6-chloro1,3-benzodioxol-5-yl)methyl)4-((1-methylethyl)thio)1H-imidazol-5-carboxylic acid M.p.=160° C.

EXAMPLE 52

2-butyl1-((6-chloro1,3-benzodioxol-5-yl)methyl)4-((4-hydroxybutyl)thio)1H-imidazol-5-carboxylic acid M.p.=135° C.

EXAMPLE 53

2-butyl 4-((carboxymethyl)thio)1-((6-chloro1,3-benzodioxol-5-yl)methyl)1H-imidazol-5-carboxylic acid M.p.=165.8° C.

EXAMPLE 54

2-butyl4-((3-carboxypropyl)thio)1-((6-chloro1,3-benzodioxol-5-yl)methyl)1H-imidazol-5-carboxylic acid M.p.=140° C.

EXAMPLE 55 ethyl(E) 3-(1-((6-chloro1,3-benzodioxol-5-yl) methyl)4-(((4-methoxyphenyl)thio)propyl 1H-imidazol-5-yl)2-propenoate 1.01 g of triethylphosphonate, 15 ml of tetrahydrofuran and 172.8 mg of sodium hydride are agitated for 5 minutes at ambient temperature. 1 g of the aldehyde obtained during the synthesis of the product of Example 32, in solution in 30 ml of tetrahydrofuran, is added and agitation is continued for 30 minutes. The solvent is evaporated off under reduced pressure, the residue is taken up in ethyl acetate, followed by washing with water, drying, the solvent is evaporated off and the crude product is recrystallized from isopropyl ether at 40° C. 1.16 g of expected product is obtained. M.p.=167.8° C.

EXAMPLE 56

(E) 3-(1-((6-chloro1,3-benzodioxol-5-yl)methyl)4-((4-methoxyphenylthio)propyl 1H-imidazol-5-yl)2-propenoic acid The operation is carried out as in Example 49 starting with 850 mg of the product obtained in Example 55, 40 ml of 2N soda and 40 ml of ethanol, leaving the reaction medium under agitation for 6 hours. After recrystallization from isopropyl ether, 745 mg of expected product is obtained.

M.p.=180.8° C.

EXAMPLE 57 methyl 1-((6-chloro1,3-benzodioxol-5-yl)methyl)4-((4-methoxyphenyl)thio) 2-propyl1H-imidazol-5-acetate

STAGE A (Cis,trans)1-((6-chloro 1,3-benzodioxol-5-yl)methyl) 4-((4-methoxyphenyl)thio)5-(2-methylsulphinyl) 2-(methylthio)ethenyl)2-propyl1H-imidazole 279 mg of methyl methylsulphinyl methyl sulphoxide and 14 mg of soda are mixed together, the mixture is agitated for 30 minutes at 70° C. and 500 mg of the aldehyde obtained during the synthesis of the product of Example 32 is added little by little. Agitation is continued at 70° C. for 2 hours, extraction is carried out with methylene chloride, followed by washing with water, drying, the solvent is evaporated offunder reduced pressure, the residue is chromatographed on silica (eluant: $CH_2Cl_2$-AcOEt 4-1) and 617 mg of expected product is obtained.

STAGE B methyl 1-((6-chloro1,3-benzodioxol-5-yl)methyl)4-((4-methoxyphenyl)thio)2-propyl1H-imidazol-5-acetate 1.02 ml of acetyl chloride in 4.1 ml of methanol is agitated for 15 minutes and is slowly added to 380 mg of the product obtained in Stage A in solution in 2 ml of methanol. The reaction medium is acidified by the addition of hydrochloric acid, agitation is carried out for 16 hours at ambient temperature, followed by neutralizing by the addition of an aqueous solution of sodium bicarbonate. Extraction is carried out with dichloromethane, the organic phase is washed with water, dried, the solvent is eliminated under reduced pressure, the residue is purified by chromatography on silica (eluant: $CH_2Cl_2$-AcOEt 95-5) and 290 mg of expected product is obtained.

$R_f$=0.66 ($CH_2Cl_2$-AcOEt 4-1).

EXAMPLE 58

1-((6-chloro1,3-benzodioxol-5-yl)methyl)4-((4-methoxyphenyl)thio)2-propyl1H-imidazol-5-acetic acid The operation is carried out as in Example 49 using 290 mg of the product obtained in the preceding example, 10 $cm^3$ of an aqueous solution of 2N sodium hydroxide and 10 $cm^3$ of methanol. After recrystallization from ethyl acetate, 193 mg of expected product is obtained. M.p.=187° C.

EXAMPLE 59 ethyl (E) 1-((6-chloro1,3-benzodioxol-5-yl)methyl) 4-(2-phenylethenyl)2-propyl1,3-imidazol-5-carboxylate 150 mg of sodium hydride is added to a suspension containing 1.2 g of benzyltriphenyl phosphonium chloride in 30 ml of tetrahydrofuran. Agitation is carried out for 30 minutes, the reaction medium is cooled down to +10° C. and 1 g of the aldehyde obtained in Example 44 in solution in tetrahydrofuran is added and agitation is continued for 2 hours at ambient temperature, followed by filtration, the organic phase is washed with tetrahydrofuran, the solvent is eliminated under reduced pressure and the residue is chromatographed on silica (eluant: $CH_2Cl_2$-AcOEt 80-20). 920 mg of expected product is obtained. M.p.=161° C.

EXAMPLE 60

(E) 1-((6-chloro1,3-benzodioxol-5-yl)methyl) 4-(2-phenylethenyl)2-propyl 1H-imidazol-5-carboxylic acid 400 mg of the product obtained in Example 59 in solution in 50 ml of ethanol and 50 ml of tetrahydrofuran and 10 ml of 2N soda is agitated for 16 hours at ambient temperature. The solvent is eliminated under reduced pressure, the residue is taken up in water, filtration is carried out, followed by acidification by the addition of 2N hydrochloric acid, the recipitate is separated off, washed with water then with ethanol, dried at 50° C. under reduced pressure and 250 mg of expected product is recovered. M.p.=230° C.

EXAMPLE 61

1-((6-chloro1,3-benzodioxol-5-yl)methyl)4-(2-phenylethyl)2-propyl1H-imidazol-5-carboxylic acid 490 mg of the product obtained in Example 58 is dissolved in a mixture containing 50 ml of ethanol and 50 ml of ethyl acetate, 50 mg of platinum oxide is added and the whole is hydrogenated under 200 g of pressure. The catalyst is separated off, the solvent is eliminated under reduced pressure, the residue is chromatographed on silica (eluant: $CH_2Cl_2$-AcOEt 95-5) and 320 mg of ethyl 1-((6-chloro 1,3-benzodioxol-5-yl)methyl)4-(2-phenylethyl)2-propyl 1H-imidazol5-carboxylate with Rf=0.22 ($CH_2Cl_2$-AcOEt 95-5) and 80 mg of totally reduced product of ethyl 1-((6-chloro 1,3-benzodioxol-5-yl)methyl)4-(2-cyclohexylethyl) 2-propyl 1H-imidazol5-carboxylate with $R_f$=0.35 are obtained.

300 mg of the partially reduced isomer is dissolved in 40 ml of ethanol, 5 ml of 2N soda is added, agitation is carried out for 16 hours at ambient temperature, followed by acidification by the addition of 2N hydrochloric acid, the solvent is eliminated under reduced pressure, the precipitate is separated off, washed with water, dried at 60° C. under reduced pressure and after impasting in isopropyl ether, 240 mg of expected product is collected. M.p.=204° C.

By operating as indicated in Examples 59 and 60, starting with the appropriate compounds, the ester and the acid of the corresponding example were obtained:

EXAMPLE 62

1-((6-chloro1,3-benzodioxol-5-yl)methyl)4-(2-cyclohexylethyl)2-propyl1H-imidazol-5-carboxylic acid M.p.=approx. 150° C.

EXAMPLE 63 ethyl 4-(((4-(2-carboxyethyl)phenyl)thio)methyl)1-((6-chloro1,3-benzodioxol-5-yl)methyl)2-propyl1H-imidazol-5-carboxylate 500 mg of the product obtained in Example 45 is dissolved in 50 ml of dichloromethane and 0.8 ml of N-ethyl diisopropylamine is added. The reaction medium is cooled down to 0° C., 0.15 ml of mesyl chloride is slowly added, agitation is carried out for one hour and 360 mg of 4-(2-carboxyethyl)phenylthiol is added and agitation is continued for 2 hours, followed by washing with water and drying, the solvent is eliminated under reduced pressure, the residue is chromatographed on silica (eluant: $CH_2Cl_2$—$CH_3OH$ 95-5) and 570 mg of expected product is obtained. M.p.=174° C.

EXAMPLE 64

4-(((4-(2-carboxyethyl)phenyl)thio)methyl)1-((6-chloro1,3-benzodioxol-5-yl)methyl)2-propyl1H-imidazol-5-carboxylic acid 540 mg of the ester obtained in Example 63 is dissolved in 20 ml of ethanol and 10 ml of 2N soda and the solution is agitated for 5 hours at ambient temperature. The solvent is evaporated off under reduced pressure, the aqueous phase is filtered off, it is acidified using acetic acid, the precipitate is separated off, washed with water, dried at 50° C. under reduced pressure. The residue is taken up in isopropyl ether, dried and 420 mg of expected product is obtained. M.p.= 171° C.

By operating as indicated in Examples 63 and 64 starting with the appropriate compounds, the esters and the acids of the following examples were prepared:

EXAMPLE 65

1-((6-chloro1,3-benzodioxol-5-yl)methyl)4-(((3,4-dimethoxyphenyl)thio)methyl)2-propyl 1H-imidazol-5-carboxylic acid M.p.=215° C.

EXAMPLE 66

1-((6-chloro1,3-benzodioxol-5-yl)methyl)4-(((4-(1-methylethyl)phenyl)thio)methyl)2-propyl1H-imidazol-5-carboxylic acid M.p.=230° C.

EXAMPLE 67

1-((6-chloro1,3-benzodioxol-5-yl)methyl)4-((4-morpholinyl)methyl)2-propyl1H-imidazol-5-carboxylic acid M.p.=104° C.

EXAMPLE 68

1-((6-chloro7-(1,2-dioxo2-ethoxyethyl)1,3-benzodioxol-5-yl)methyl)4-((3-dimethoxyphenyl)thio) 2-propyl 1H-imidazol5-carboxylic acid 350 mg of the acid obtained in Example 34 is dissolved in 30 ml of tetrahydrofuran, the solution is cooled down to −78° C. and 1.05 ml of n-butyllithium is added. Agitation is carried out for 5 minutes, 0.48 ml of diethyl oxalate is added and agitation is continued for one hour at ambient temperature. The reaction medium is hydrolyzed by the addition of water, acidified by the addition of 2N hydrochloric acid, extraction is carried out with ethyl acetate, the organic phase is washed with water, dried, the solvent is eliminated, the residue is chromatographed on silica (eluant: $CH_2Cl_2$—$CH_3OH$ 95-5) and 210 mg of expected product is obtained. $R_f$=0.25 ($CH_2Cl_2$—$CH_3OH$ 95-5).

EXAMPLE 69

Potassium salt of 1-((6-chloro7-(carboxycarbonyl)1,3-benzodioxol-5-yl)methyl)4-((3,4-dimethoxyphenyl)thio)2-propyl1-imidazol 5-carboxylic acid 5 ml of 2N soda is added to 190 mg of the product obtained in Example 68 in solution in 10 ml of ethanol and agitation is carried out for 16 hours at ambient temperature. The ethanol is eliminated under reduced pressure, the aqueous phase is acidified by the addition of 2N hydrochloric acid, the precipitate is separated off, washed with water, dried under reduced pressure. The residue is taken up in ethanol, alkalinization is carried out by the addition of potash in 10 ml of isopropanol, the crystallized product is separated off and dried at 50° C. under reduced pressure. 70 mg of expected product is obtained. M.p.>260° C.

By operating as indicated in Example 54, starting with the appropriate compounds, the products of the following examples were prepared:

EXAMPLE 70

2-propyl4-((3-carboxypropyl)thio)1-((6-chloro1,3-benzodioxol-5-yl)methyl)1H-imidazol5-carboxylic acid M.p.=154° C.

EXAMPLE 71

2-propyl4-((7-carboxyheptyl)thio)1-((6-chloro1,3-benzodioxol-5-yl)methyl)1H-imidazol5-carboxylic acid M.p.=133° C.

EXAMPLE 72 of pharmaceutical composition.

Tablets were prepared corresponding to the following formula:

| | |
|---|---|
| Product of Example 7 | 50 mg |
| Excipient for a tablet made up to | 200 mg |

PHARMACOLOGICAL RESULTS

STUDY OF THE ACTIVITY ON THE B RECEPTOR OF ENDOTHELIN

A membrane preparation is produced from the posterior cortex plus cerebellum of a rat. The tissue is ground up in a POLYTRON in a 50 mM Tris buffer pH=7.4.

After 30 minutes at 25° C. (W.B.) the homogenate is centrifuged at 30000 g for 15 minutes (2 centrifugations with intermediate take-up in the Tris buffer pH. 7.4).

The pellets are resuspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquots are distributed into hemolysis tubes and $^{125}$I Endothelin (approximately 50000 dpm/tube) and the product to be studied are added. (The product is first tested at $3\times10^{-5}$M three times). When the tested product displaces more than 50% of the radioactivity specifically bound to the receptor, it is tested again according to a range of 7 concentrations so as to determine the concentration which inhibits the radioactivity specifically bound to the receptor by 50%. In this way the 50% inhibitory concentration is determined.

The non-specific bond is determined by the addition of $10^{-6}$M endothelin (three times). After incubation at 25° C. for 60 minutes, putting back in the water bath at 0° C., for 5 minutes, filtering under reduced pressure, rinsing with Tris buffer 7.4, the radioactivity is counted in the presence of scintillating Triton.

The result is expressed directly as the 50% inhibitory concentration (IC50), that is to say as the concentration of product studied expressed in nM, necessary to displace 50% of the specific radioactivity bound to the receptor studied.

Result

The IC50's found for the products of the examples are given in Table I hereafter, in nanomoles.

Results

TABLE I

| Product of examples | B receptor of endothelin IC/50 in nanomoles |
|---|---|
| 10 | 250 |
| 21 | 350 |

STUDY OF THE ACTIVITY ON THE A RECEPTOR OF ENDOTHELIN

A membrane preparation is produced from the heart (ventricles) of a rat. The tissue is ground up in a POLYTRON in a 50 mM Tris buffer pH=7.4.

After 30 minutes at 25° C. (W.B.) the homogenate is centrifuged at 30000 g for 15 minutes (2 centrifugations with intermediate take up in the Tris buffer pH. 7.4).

The pellets are resuspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquots are distributed into hemolysis tubes and $^{125}$I Endothelin (approximately 50000 dpm/tube) and the product to be studied are added. (The product is first tested at 3×10⁻⁵M three times). When the tested product displaces more than 50% of the radioactivity specifically bound to the receptor, it is tested again according to a range of 7 concentrations so as to determine the concentration which inhibits the radioactivity specifically bound to the receptor by 50%. In this way the 50% inhibitory concentration is determined.The non-specific bond is determined by the addition of 10⁻⁶M endothelin (three times). After incubation at 25° C. for 60 minutes, putting back in the water bath at 0° C., for 5 minutes, filtering under reduced pressure, rinsing with Tris buffer 7.4, the radioactivity is counted in the presence of scintillating Triton.The result is expressed directly as the 50% inhibitory concentration (IC50), that is to say as the concentration of product studied expressed in nM, necessary to displace 50% of the specific radioactivity bound to the receptor studied.
ResultThe IC50's found for the products of the examples are given in Table I hereafter, in nanomoles.
Results

TABLE I

| Product of examples | A receptor of endothelin IC/50 in nanomoles |
|---|---|
| 10 | 91 |
| 21 | 110 |

What is claimed is:1. A method of reducing abnormal stimulation of endothelin receptors in warm-blooded animals comprising administering to warm-blooded animals in need thereof an amount sufficient to reduce stimulation of endothelin receptors of a compound in all possible racemic, enantiomeric and diastereomeric forms selected from the group consisting of a compound of the formula

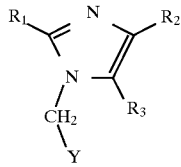

wherein $R_1$ is selected from the group consisting of hydroxyl and alkyl, alkenyl, alkynyl, alkoxy and alkylthiol of up to 12 carbon atoms, formyl and cycloalkyl of 3 to 7 carbon atoms ring interrupted with at least one heteroatom selected from the group consisting of oxygen, sulfur, and nitrogen or not interrupted, all unsubstituted or substituted with at least one member selected from the group consisting of halogen, —OH, carboxy, carboxy esterified with an alkanol of 1 to 6 carbon atoms, —CONH₂, carboxy salified with a base, —CN, —NO₂, —NH₂, mono and di-alkylamino of 1 to 6 alkyl carbon atoms, alkyl of 1 to 6 carbon atoms, cycloalkyl of 3 to 7 carbon atoms, alkyl of 1 to 6 carbon atoms, alkoxy of 1 to 6 carbon atoms, alkenyl of 2 to 6 carbon atoms, haloalkyl of 1 to 6 carbon atoms, haloalkoxy of 1 to 6 carbon atoms, haloalkylthio of 1 to 6 carbon atoms, alkylthio of 1 to 6 carbon atoms, phenoxy, phenylalkoxy of 1 to 6 alkyl carbon atoms, carbamoyl, acyl of an organic carboxylic acid of 1 to 6 carbon atoms, acyloxy of an organic carboxylic acid of 1 to 6 carbon atoms, tetrazolyl, tetrazolyl salified with a base and phenyl unsubstituted or substituted with at least one member of the group consisting of halogen, —OH, alkyl of 1 to 4 carbon atoms, alkoxy of 1 to 4 carbon atoms, —CF₃, —CN, carboxy, carboxy salified with a base, carboxy esterified with alkanol of 1 to 6 carbon atoms and tetrazolyl, $R_2$ and $R_3$ are individually selected from the group consisting of a) halogen, —SH, acyl of an organic carboxylic acid of 1 to 6 carbon atoms, carboxy, —CONH₂, carboxy salified with a base, carboxy esterified with an alkanol of 1 to 6 carbon atoms, carboxy carbonyl, —NO₂, —CN and —P(O) (OR)₂ and R is selected from the group consisting of hydrogen, alkyl of 1 to 4 carbon atoms and phenyl, b) $R_4$ and —$OR_4$ wherein $R_4$ is —$(CH_2)_{m1}$—S(O)$_{m2}$—X—$R_{10}$ wherein m1 is an integer from 0 to 4, m2 is an integer from 0 to 2 and —$XR_{10}$ is amino or X is selected from the group consisting of a single bond, —$NR_{11}$, —$NR_4$—CO—, —$NR_{11}$COO, —$NR_{11}$—$CON_{R12}$— and —N=$CR_{11}$—$NR_{12}$, $R_{10}$ is selected from the group consisting of alkyl of 1 to 6 carbon atoms, alkenyl of up to 6 carbon atoms and aryl, all unsubstituted or substituted with at least one member of the group consisting of a) —OH, cycloalkyl of 3 to 7 carbon atoms, b) alkyl, alkoxy, haloalkyl, alkylthio, haloalkylthio and haloalkoxy of 1 to 6 carbon atoms, c) phenoxy, phenylalkoxy of 1 to 6 alkyl carbon atoms, carbamoyl, acyl of an organic carboxylic acid of 1 to 6 carbon atoms, acyloxy of an organic carboxylic acid of 1 to 6 carbon atoms, carboxy, carboxy salified with a base, carboxy esterified with an alkanol of 1 to 6 carbon atoms, tetrazolyl, —CN, —NO₂, —NH₂, mono and dialkylamino of 1 to 6 carbon atoms and aryl substituted with at least one member of the group consisting of halogen, —OH, alkyl and alkoxy of 1 to 4 carbon atoms, —CF₃, tetrazolyl, carboxy salified with a base and carboxy esterified with an alkanol of 1 to 6 carbon atoms and $R_{11}$ and $R_{12}$ are individually hydrogen or a value of $R_{10}$ or $R_4$ is selected from the group consisting of a) hydrogen, b) alkyl, alkenyl, alkynyl and acyl of an organic carboxylic acid, all up to 6 carbon atoms uninterrupted or interrupted by at least one heteroatom selected from the group consisting of oxygen, sulfur and nitrogen, c) amino and carbamoyl unsubstituted or substituted with 1 to 2 alkyl and alkynyl of up to 6 carbon atoms, d) —$(CH_2)_{m1}$—S(O)$_{m2}$—$XR_{10}$ as defined above and e) cycloalkyl of 3 to 6 carbon atoms and aryl with the alkyl, alkenyl and aryl of $R_4$ being unsubstituted or substituted by at least one member of the group consisting of a) halogen, —OH, —SH, —CN, azido, —NO₂, —SO₃H, carboxy, carboxy salified with a base, carboxyl esterified with an alkanol of 1 to 6 carbon atoms and amidified carboxy, b) alkyl, alkenyl, alkoxy, haloalkyl, alkylthio, alkenylthio, alkynylthio, haloalkylthio, haloalkoxy, and acyl of an organic carboxylic acid of 1 to 6 carbon atoms, acylthio of an organic carboxylic acid of 1 to 6 carbon atoms, and acyloxy of an organic carboxylic acid, all of up to 6 carbon atoms, c) aryl, arylthio, aralkyl, aralkenyl, aryloxy and arylalkoxy wherein the aryl is unsubstituted or substituted by at least one member of the group consisting of halogen, —OH, alkyl and alkoxy of 1 to 6 carbon atoms, haloalkyl, alkylthio, haloalkylthio, haloalkoxy, carbamoyl, acyl of an organic carboxylic acid of 1 to 6 carbon atoms, acyloxy of an organic carboxylic acid of 1 to 6 carbon atoms, carboxy, carboxy salified with a base, carboxy esterified with an alkanol of 1 to 6 carbon atoms, —CN, —NO₂, —NH₂, mono and dialkylamino of 1 to 6 alkyl carbon atoms, tetrazolyl and phenyl unsubstituted or substituted with at least one member of the group consisting of halogen, —OH, alkyl and alkoxy of 1 to 4 carbon atoms, —CF₃, tetrazolyl, carboxy, carboxy salified with a base and carboxy esterified with an alkanol of 1 to 6 carbon atoms and tetrazolyl

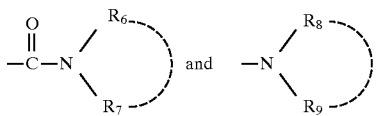

wherein $R_6$ and $R_7$ and $R_8$ and $R_9$ are individually selected from the group consisting of a) hydrogen, amino acids, b) alkyl and alkenyl of up to 6 carbon atoms unsubstituted or substituted by at least one member of the group consisting of halogen, —OH and alkoxy of 1 to 6 carbon atoms, c) aryl, aralkyl and arylalkenyl of up to 6 alkyl carbon atoms unsubstituted or substituted by at least one member of the group consisting of halogen, —OH, —CN, —NO₂, alkyl, alkenyl, haloalkyl, alkoxy and acyl of an organic carboxylic acid, all alkyl of up to 6 carbon atoms, —NH₂, mono and dialkylamino of 1 to 6 alkyl carbon atoms, carboxy, carboxy salified with a base and carboxy esterified with an alkanol of 1 to 6 carbon atoms and aryl and aralkyl, the last two unsubstituted or substituted with at least one member of the group consisting of halogen, —OH, —CF₃, —NO₂, —CN, tetrazolyl, carboxy, carboxy salified with a base and carboxy esterified with an alkanol of 1 to 6 carbon atoms and d) —(CH₂)$_{m1}$—S(O)$_{m2}$—XR₁₀ defined as above or R₆ and R₇ or R₈ and R₉ together with the nitrogen to which they are attached form a heterocycle selected from the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thomorpholinyl, azepine, indolyl, all unsubstituted or substituted by at least one member of the group consisting of halogen, hydroxyl, nitro, cyano, acyl, trifluoromethyl, alkyl of 1 to 4 carbon atoms, alkoxy of 1 to 4 carbon atoms, free carboxy, carboxy salified with a base, carboxy esterified with alkanol of 1 to 6 carbon atoms,

tetrazolyl, oxazolyl and phenyl, or R₈ and R₉ are individually acyl of an organic carboxylic acid of 1 to 6 carbon atoms or one of R₈ and R₉ is carbamoyl or alkoxycarbonyl or benzyloxycarbonyl and the other is R₈ as defined above or R₈ or R₉ together with the nitrogen atom form phthalimido or succinimido, Y is —Y₁—B—Y₂, Y₁ is aryl unsubstituted or substituted with dioxol or one of R₂ and R₃, B is a single bond or a member of the group consisting of

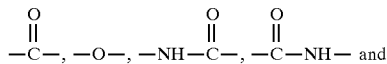

is a single bond, Y₂ is selected from the group consisting of hydrogen, alkoxy of 1 to 6 carbon atoms, halogen, —CN, tetrazolyl, carboxy, carboxy salified with a base, carboxy amidified, carboxy esterified with an alkanol or 1 to 6 carbon atoms and —(CH₂)$_{m1}$—S(O)$_{m2}$—XR₁₀ defined as above and their non-toxic, pharmaceutically acceptable acid addition salts. 2. The method of claim 1 wherein Y is benzofuranyl or phenyl substituted by oxal and unsubstituted or substituted with one of R₂ or R₃. 3. The method of claim 1 having the formula wherein the compound has the formula

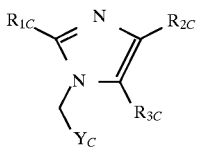

wherein R$_{1C}$ is selected from the group consisting of alkyl of 1 to 4 carbon atoms unsubstituted or substituted by —OH or alkoxy of 1 to 6 carbon atoms, alkylthio of 1 to 6 carbon atoms, dioxolane and dioxane, R$_{2C}$ is selected from the group consisting of

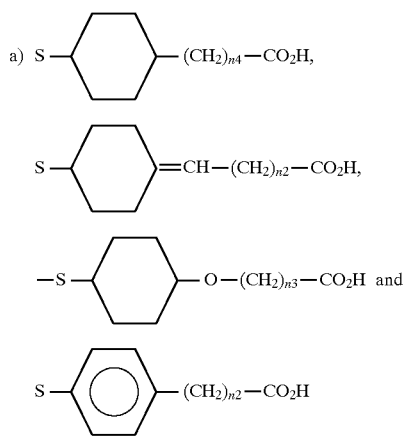

wherein n₃ is 1, 2 or 3, n₄ is 2 or 3, b) alkylthio, alkenylthio, cycloalkylthio, cycloalkyl, cycloalkylalkyl and cycloalkylalkenyl with alkyl and alkenyl of up to 6 carbon atoms, phenyl phenoxy, phenylthio, benzyl, benzoyl and phenylthioalkyl, all unsubstituted or substituted with at least one member of the group consisting of —OH, carboxy and alkyl, alkenyl and alkoxy of up to 4 carbon atoms unsubstituted or substituted by carboxy with the phenyl optionally substituted with dioxol on 2 adjacent carbon atoms, R$_{3C}$ is selected from the group consisting of carboxy, carboxy esterified with an alkanol of 1 to 6 carbon atoms, tetrazolyl and sulfonylamino, Y$_C$ is phenyl substituted with dioxol and unsubstituted or with at least one member of the group consisting of halogen, —OH, carboxy and alkoxy of 1 to 4 carbon atoms. 4. The method of claim 1 selected from the group consisting of 1-((6-chloro-1,3-benzodioxol-5-yl)-methyl)-4-(4-methoxy-benzylthio)-1H-imidazole-5-carboxylic acid, 2-butyl-1-((6-chloro-1,3-benzodioxol-5-yl)-methyl)-5-((4-methoxy-phenyl)-thio)-1H-imidazole-4-carboxylic acid, 1-((6-chloro-1,3-benzodioxol-5-yl)-methyl)-2,4-bis-(4-methoxybenzylthio)-1H-imidazole-5-carboxylic acid, 1-((6-chloro-1,3-benzodioxol-5-yl)-methyl)-4-(4-methoxyphenyl)-thio)-2-(propylthio)-1H-imidazole-5-carboxylic acid, 1- ((6-chloro-1,3-benzodioxol-5-yl)-methyl)-4-((3,4-dimethoxyphenyl)-thio)-2-propyl-1H-imidzole-5-carboxylic acid, 2-butyl-1-((6-chloro-1,3-benzodioxol-5-yl)-methyl)-4-(cyclohexylthio)-1H-imidazole-5-carboxylic acid, 2-butyl-4-((3-carboxypropyl)-thio)-1-((6-chloro-1,3-benzodioxol-5-yl)-methyl)-1H-imidzole-5-carboxylic acid, 4-(((4-(2-carboxyethyl)-phenyl)-thio)-methyl)-1-((6-chloro-1,3-benzodioxol-5-yl)-methyl)-2-propyl-1H-imidazol-5-carboxylic acid, 4-((3-carboxypropyl)-thio)-1-((6-chloro-1,3-benzodioxol-5-yl)-methyl)-2-propyl-1H-imidazol-5-carboxylic acid and 4-((7-carboxyheptyl)-thio)-1-((6-chloro-1,3-benzodioxol-5-yl) -methyl) -2-propyl-1H-imidazol-5-carboxylic acid.

* * * * *